US011925655B2

(12) United States Patent
Bachovchin et al.

(10) Patent No.: US 11,925,655 B2
(45) Date of Patent: *Mar. 12, 2024

(54) FAP-ACTIVATED THERAPEUTIC AGENTS, AND USES RELATED THERETO

(71) Applicant: Bach Biosciences, LLC, Cambridge, MA (US)

(72) Inventors: William W. Bachovchin, Cambridge, MA (US); Hung-sen Lai, Andover, MA (US); David G. Sanford, Reading, MA (US); Sarah E. Poplawski, Belmont, MA (US); Wengen Wu, Winchester, MA (US)

(73) Assignee: Bach Biosciences, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/653,565

(22) Filed: Mar. 4, 2022

(65) Prior Publication Data

US 2022/0296621 A1 Sep. 22, 2022

Related U.S. Application Data

(63) Continuation of application No. 16/894,227, filed on Jun. 5, 2020, now Pat. No. 11,266,669, which is a continuation of application No. 16/161,170, filed on Oct. 16, 2018, now Pat. No. 10,709,722, which is a continuation of application No. 15/655,317, filed on Jul. 20, 2017, now Pat. No. 10,117,887, which is a continuation of application No. 15/318,607, filed as application No. PCT/US2015/035800 on Jun. 15, 2015, now Pat. No. 9,737,556.

(60) Provisional application No. 62/012,003, filed on Jun. 13, 2014.

(51) Int. Cl.
| *A61K 47/62* | (2017.01) |
| *A61K 31/704* | (2006.01) |
| *A61K 47/54* | (2017.01) |
| *A61K 47/64* | (2017.01) |

(52) U.S. Cl.
CPC .......... *A61K 31/704* (2013.01); *A61K 47/545* (2017.08); *A61K 47/62* (2017.08); *A61K 47/64* (2017.08)

(58) Field of Classification Search
None
See application file for complete search history.

(56) References Cited

U.S. PATENT DOCUMENTS

| 5,433,955 A | 7/1995 | Bredehorst et al. |
| 5,571,785 A | 11/1996 | Angelucci et al. |
| 6,531,474 B1 | 3/2003 | Wannamaker et al. |
| 6,613,879 B1 | 9/2003 | Firestone et al. |
| 7,115,573 B2 | 10/2006 | Pickford et al. |
| 7,304,037 B2 | 12/2007 | Lerchen et al. |
| 7,754,681 B2 | 7/2010 | Feng |
| 8,993,295 B2 | 3/2015 | Seed et al. |
| 9,597,410 B2 | 3/2017 | Bachovchin et al. |
| 9,737,556 B2 | 8/2017 | Bachovchin et al. |
| 10,117,887 B2 | 11/2018 | Bachovchin et al. |
| 10,245,248 B2 | 4/2019 | Bachovchin et al. |
| 10,709,722 B2 | 7/2020 | Bachovchin et al. |
| 11,266,669 B2 | 3/2022 | Bachovchin et al. |
| 2002/0155565 A1 | 10/2002 | Garin-Chesa et al. |
| 2003/0055052 A1 | 3/2003 | Peters et al. |
| 2003/0232742 A1 | 12/2003 | Peters et al. |
| 2004/0033957 A1 | 2/2004 | Patzelt et al. |
| 2014/0087991 A1 | 3/2014 | Denmeade et al. |
| 2015/0265572 A1 | 9/2015 | Chen et al. |
| 2017/0119901 A1 | 5/2017 | Bachovchin et al. |
| 2017/0128476 A1 | 5/2017 | Bachovchin et al. |
| 2017/0247476 A1 | 8/2017 | Yan et al. |
| 2020/0016114 A1 | 1/2020 | Bachovchin et al. |

FOREIGN PATENT DOCUMENTS

| EP | 1333033 A1 | 8/2003 |
| JP | 2003500417 A | 1/2003 |
| JP | 2008517917 A | 5/2008 |
| WO | WO 2000/071571 A2 | 11/2000 |
| WO | WO 02/38590 | 5/2002 |
| WO | WO 2002/100353 A2 | 12/2002 |
| WO | WO 2003/094972 A2 | 11/2003 |

(Continued)

OTHER PUBLICATIONS

Ozkan, et al., Gemcitabine and Cisplatin Combination Chemotherapy in Triple Negative Metastatic Breast Cancer Previously Treated with a Taxane/Anthracycline Chemotherapy; Multicenter Experience, Neoplasma 59, 1, 2012. (Year: 2012).*

Extended European Search Report issued by the European Patent Office in corresponding Application No. 15807049.0, dated Jan. 4, 2018.

International Search Report and Written Opinion for International Application No. PCT/US2015/035798 dated Sep. 1, 2015.

International Search Report for International Application No. PCT/US2015/035800 dated Sep. 15, 2015.

(Continued)

*Primary Examiner* — Thomas S Heard
(74) *Attorney, Agent, or Firm* — Lathrop GPM LLP; Brian C. Trinque

(57) ABSTRACT

Disclosed are prodrugs of anthracyclines (such as doxorubicin) and derivatives thereof that are selectively cleaved and activated by fibroblast activating protein (FAP). The prodrugs are useful for targeted delivery of "warhead" anthracycline or anthracycline derivative to FAP-expressing tissues, including cancer (e.g., solid tumors). Also provided are pharmaceutical compounds comprising the prodrugs, as well as methods of using the prodrugs to treat a disorder characterized by FAP upregulation, e.g., cancer undesirable fibrosis and undesirable inflammation.

20 Claims, 18 Drawing Sheets

(56) References Cited

FOREIGN PATENT DOCUMENTS

| WO | WO 2008/116053 A2 | 9/2008 |
| WO | WO 2013/033396 A2 | 3/2013 |
| WO | WO 2014/102312 A2 | 7/2014 |
| WO | WO 2015/192123 A1 | 12/2015 |
| WO | WO 2015/192124 A1 | 12/2015 |
| WO | WO 2017/173347 A1 | 10/2017 |
| WO | WO 2017/189569 A1 | 11/2017 |

OTHER PUBLICATIONS

Poplawski, S. et al. Identification of selective and potent inhibitors of fibroblast activation protein and prolyl oligopeptidase. *J. Med. Chem.* 2013, 56, 3467-3477.

Scanlan et al., "Molecular cloning of fibroblast activation protein α, a member of the serine protease family selectively expressed in stromal fibroblasts of epithelial cancers", *PNAS USA* 91(12):5657-5661 (1994).

\* cited by examiner

FAP-ACTIVATED THERAPEUTIC AGENTS, AND USES RELATED THERETO

RELATED APPLICATION

This application is a continuation of U.S. patent application Ser. No. 16/894,227, filed Jun. 5, 2020, now U.S. Pat. No. 11,266,669, which is a continuation of U.S. patent application Ser. No. 16/161,170, filed Oct. 16, 2018, now U.S. Pat. No. 10,709,722, which is a continuation of U.S. patent application Ser. No. 15/655,317, filed Jul. 20, 2017, now U.S. Pat. No. 10,117,887, which is a continuation of U.S. patent application Ser. No. 15/318,607, filed Dec. 13, 2016, now U.S. Pat. No. 9,737,556, which is 35 U.S.C. § 371 filing of International Patent Application No. PCT/US2015/035800, filed Jun. 15, 2015, which claims the benefit of U.S. Provisional Patent Application No. 62/012,003, filed Jun. 13, 2014.

BACKGROUND

Cancer is characterized by cell proliferation without normal regulation by external signals, and the potential to invade and metastasize to other tissues. For many years chemotherapy has been a mainstay of treatment for various types of cancer. Conventional chemotherapy works essentially by poisoning rapidly dividing cells. As such, it has relatively low selectivity for cancer cells per se, resulting in the familiar side effects of hair loss, diarrhea and other forms of gastrointestinal upset, and marrow suppression. Such off-target side effects frequently become dose-limiting, and typically impose a constraint on treatment efficacy.

For example, doxorubicin, also known as hydroxydaunorubicin, is a drug used in cancer chemotherapy. It is an anthracycline antibiotic, closely related to the natural product daunomycin. Like all anthracyclines, it works by intercalating DNA, with the most serious adverse effect being life-threatening heart damage. Doxorubicin is commonly used in the treatment of a wide range of cancers, including hematological malignancies, many types of carcinoma, and soft tissue sarcomas.

Anticancer therapy would be greatly improved if it were selectively targeted to cancer cells. Many approaches have been proposed and developed with the goal of achieving selective targeting of cancer treatment agents. For example, cytotoxic agents have been linked to monoclonal antibodies and antigen-specific fragments thereof which are capable of binding specifically to certain tumor antigens.

The effect of folate-targeted liposomal doxorubicin (FTL-Dox) has been well characterized in folate receptor (FR)-overexpressing tumors in vitro, particularly in KB human carcinoma cells. Riviere et al. *J Drug Targeting* 19(1):14-24 (2011) investigated the antitumor activity of FTL-Dox injected intravenously into mice bearing KB tumors. Mice were administered a single intravenous injection of free Dox, nontargeted PEGylated liposomal Dox (PL-Dox), or FTL-Dox. FTLs and PLs accumulated similarly in tumor tissue, despite the faster clearance of FTLs from circulation. Mice treated with FTL-Dox (20 mg/kg) displayed greater inhibition of tumor growth, and almost a 50 percent increase in life span, compared to mice receiving PL-Dox (20 mg/kg). Riviere et al. concluded that while FTLs administered systemically have the potential to enhance the delivery of anticancer drugs in vivo, their removal by FR-expressing normal tissues may have to be blocked if the benefits of tumor targeting are to be realized.

Membrane-bound proteases have recently emerged as critical mediators of tumorigenesis, angiogenesis, and metastasis. Fibroblast activation protein alpha (FAPα, or simply FAP; EC 3.4.21.-), also known as seprase or 170 kDa melanoma membrane-bound gelatinase, is a homodimeric integral membrane protein belonging to the serine protease family. Scanlan et al. (1994) *Proc Natl Acad Sci USA* 91:5657-61; and WO 97/34927 (incorporated by reference).

Normal adult tissues generally do not express detectable amounts of FAP. In contrast, FAP is expressed in reactive stromal fibroblasts of epithelial cancers, granulation tissue of healing wounds, and malignant cells of bone and soft tissue sarcomas. FAP is thought to be involved in the control of fibroblast growth or epithelial-mesenchymal interactions during development, tissue repair, and epithelial carcinogenesis. Significantly, most common types of epithelial cancers, including more than 90 percent of breast, non-small cell lung, and colorectal carcinomas, contain FAP-expressing stromal fibroblasts. Scanlan et al. *Proc Natl Acad Sci USA* 91:5657-61 (1994). Because in adults its expression is restricted to pathologic sites, including cancer, fibrosis, arthritis, wounding, and inflammation, FAP can provide target specificity to therapeutic agents.

U.S. Pat. No. 6,613,879 (incorporated by reference) to Firestone et al. discloses a prodrug that is capable of being converted into a cytotoxic or cytostatic drug by catalytic action of human FAP. The prodrug includes a cleavage site which is recognized by FAP.

PCT Publication WO 2013/033396 (incorporated by reference) discloses a FAP-activated prodrug of a proteasome inhibitor, wherein the proteasome inhibitor is linked to a FAP substrate, such that when the proteasome inhibitor is released from the prodrug as a result of cleavage by FAP, the proteasome inhibitor inhibits the proteolytic activity of a proteasome with a Ki of 500 nM or less.

SUMMARY OF THE INVENTION

One aspect of the invention is a prodrug of an anthracycline or anthracycline derivative which is selectively cleaved and activated by fibroblast activating protein (FAP). In certain embodiments, the invention provides prodrugs of doxorubicin which are selectively cleaved and activated by FAP. In certain embodiments, the invention provides prodrugs of anthracyclines (such as doxorubicin) which are selectively cleaved and activated by FAP relative to (i.e., but not by) prolyl endopeptidase EC 3.4.21.26 (PREP).

In certain embodiments, the invention provides a prodrug for fibroblast activation protein (FAP)-dependent release of an active drug agent, comprising an FAP substrate covalently linked to a drug agent via a bond or a self-immolative linker. Upon cleavage by FAP of the FAP substrate, the drug agent is released in its active form or in a form that is readily metabolized to its active form. The prodrug has less than 50% of the therapeutic activity of the active form of the drug agent, and more preferably less than 60%, 70%, 80%, 90%, 95%, or even 98%. The FAP substrate has a $k_{cat}/K_m$ for cleavage by FAP at least 10-fold greater than for cleavage by prolyl endopeptidase (EC 3.4.21.26; PREP), and even more preferably at least 100-fold, 1000-fold, 5000-fold, or even 10,000-fold greater $k_{cat}/K_m$.

In certain embodiments, the prodrug may be further characterized by one or more of the following features:
  the prodrug has a therapeutic index that is at least 2 times greater than the therapeutic index of the agent, and more preferably at least 5, 10, 50, 100, 250, 500, 1000, 5000, or even 10,000 times greater;

a larger percentage of the active drug agent is localized in the target tissue, i.e., the tissue expressing FAP, relative to the administration of the agent alone, when compared on an equivalent dose basis—i.e., the ratio of active drug agent localized to the target tissue relative to other tissue (such as blood, liver or heart) is at least 2 times greater for an equivalent dose of the prodrug relative to the agent alone, and preferably at least 5, 10, 100, or even 1000 times greater;

the maximum tolerated dose of the prodrug is at least 2 times greater than the maximum tolerated dose of the agent alone, and even more preferably at least 5, 10, 100, or even 1000 times greater;

the cell permeability of the prodrug is at least 50% less than the cell permeability of the agent, and even more preferably at least 60%, 70%, 80%, 90%, 95%, 98%, 99%, or even 99.9% less; and/or the circulating half-life of the prodrug is at least 25% longer than the circulating half-life of the agent alone, and even more preferably at least 50%, 75%, 100%, 150%, 200%, 500%, 750%, or even 1000% longer.

In one embodiment, the prodrug is represented by the general formula

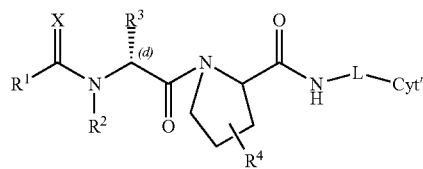

or a pharmaceutically acceptable salt thereof, wherein:
R$^1$ represents (C$_1$-C$_{10}$)alkyl, (C$_1$-C$_{10}$)alkoxy (e.g., tert-butyloxy), (C$_1$-C$_{10}$)alkyl-C(O)—(C$_1$-C$_{10}$)alkyl, (C$_3$-C$_8$)cycloalkyl, (C$_3$-C$_8$)cycloalkyl(C$_1$-C$_{10}$)alkyl, aryl, aryl(C$_1$-C$_{10}$)alkyl, heteroaryl, or heteroaryl(C$_1$-C$_{10}$)alkyl, wherein any R$^1$ is optionally substituted with one or more substituents independently selected from the group consisting of halo, hydroxy, carboxylate, cyano, amino, nitro, and thio (—SH); or —C(=X)R$^1$ represents an N-terminally blocked alpha amino acid residue and X is O;

R$^2$ represents H or a (C$_1$-C$_6$)alkyl;
R$^3$ represents H or a (C$_1$-C$_6$)alkyl;
R$^4$ is absent or represents one, two, or three substituents, each independently selected from the group consisting of (C$_1$-C$_6$)alkyl, —OH, —NH$_2$, and halogen;
X represents O or S;
Cyt', alone or in combination with -L-NH, represents an anthracycline or derivative thereof, less a hydrogen atom; and
L represents a 4-8 member ring or a large hydrophobic group which is part of the anthracycline or derivative thereof and is recognized by FAP as a P'$_1$ residue; or L is a self-immolative linker which is metabolized after FAP cleavage to release Cyt',
wherein the prodrug is selectively converted in vivo to the anthracycline or derivative thereof by FAP$^+$ stromal cells.

Without meaning to be bound to any particular theory or mechanism of action, the inventors believe the prodrugs disclosed herein are cleaved in situ by FAP to release anthracycline or related compounds, which then undergo spontaneous transformation into anthracycline or related compounds, thereby achieving targeted delivery to FAP-expressing cells of the anthracycline or anthracycline derivative.

An aspect of the invention is a prodrug represented by Formula I

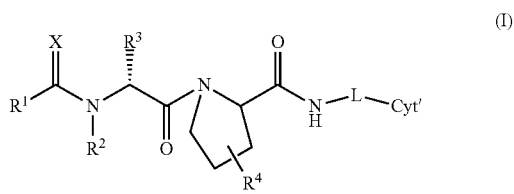

or a pharmaceutically acceptable salt thereof, wherein:
R$^1$ represents (C$_1$-C$_{10}$)alkyl, (C$_1$-C$_{10}$)alkoxy (e.g., tert-butyloxy), (C$_1$-C$_{10}$)alkyl-C(O)—(C$_1$-C$_{10}$)alkyl, (C$_3$-C$_8$)cycloalkyl, (C$_3$-C$_8$)cycloalkyl(C$_1$-C$_{10}$)alkyl, aryl, aryl(C$_1$-C$_{10}$)alkyl, heteroaryl, or heteroaryl(C$_1$-C$_{10}$)alkyl, wherein any R$^1$ is optionally substituted with one or more substituents independently selected from the group consisting of halo, hydroxy, carboxylate, cyano, amino, nitro, and thio (—SH); or —C(X)R$^1$ represents an N-terminally blocked alpha amino acid residue, wherein X is O;

R$^2$ represents H or a (C$_1$-C$_6$)alkyl;
R$^3$ represents H or a (C$_1$-C$_6$)alkyl;
R$^4$ is absent or represents a (C$_1$-C$_6$)alkyl, —OH, —NH$_2$, or halogen;
X represents O or S;
L represents a bond, or —N(H)-L- represents a self-immolative linker; and
Cyt' represents a radical of an anthracycline or derivative thereof.

An aspect of the invention is a pharmaceutical composition, comprising a prodrug of the invention, or a pharmaceutically acceptable salt thereof; and a pharmaceutically acceptable carrier.

An aspect of the invention is a method of treating a disorder characterized by fibroblast activation protein (FAP) upregulation, comprising administering to a subject in need thereof a therapeutically effective amount of a prodrug of the invention, or a pharmaceutically acceptable salt thereof.

In an embodiment, the disorder characterized by FAP upregulation is selected from the group consisting of cancer (e.g., solid tumors), fibrosis, and inflammation.

An aspect of the invention is a method of treating cancer, comprising administering to a subject in need thereof a therapeutically effective amount of a prodrug of the invention, or a pharmaceutically acceptable salt thereof.

DETAILED DESCRIPTION OF THE INVENTION

Figure 1:
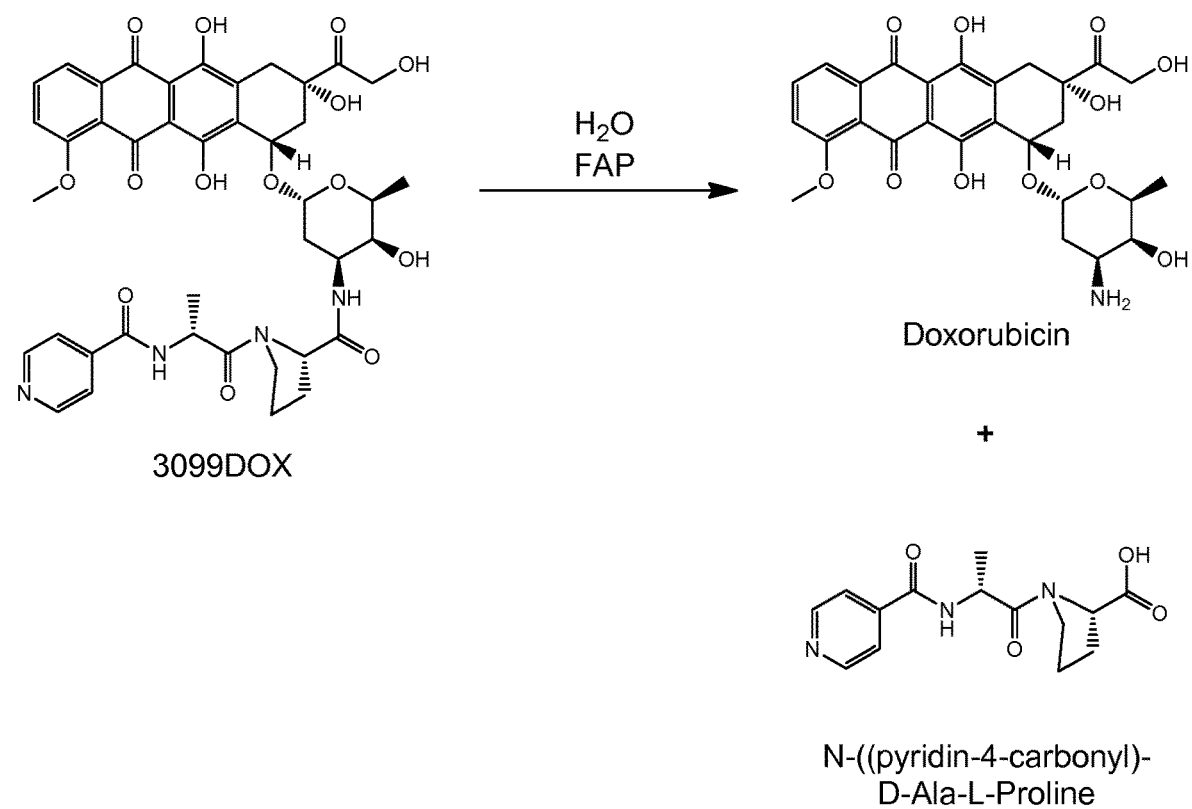
FIG. 1 depicts 3099DOX and its activation by FAP.

Fibroblast activation protein (FAP) is a post-prolyl cleaving serine protease belonging to the dipeptidyl peptidase (DPP-IV)-like subfamily. FAP and prolyl endopeptidase (PREP; EC 3.4.21.26) are the only known mammalian proteases that can cleave on the C-terminal side of an internal proline residue. FAP's $P_4$-$P_1$ cleavage specificity requires proline at $P_1$, and glycine or a D-amino acid at $P_2$, prefers small uncharged amino acids at $P_3$, and tolerates most amino acids at $P_4$. PREP, unlike FAP, is constitutively and ubiquitously expressed.

The invention exploits the enzymatic activity and specificity of FAP, and the properties of self-immolative linkers, to provide non-cytotoxic, non-cytostatic prodrugs that are capable of targeting delivery of anthracycline compounds to FAP-expressing cells, e.g., reactive stromal fibroblasts of epithelial cancers, granulation tissue of healing wounds, and malignant cells of bone and soft tissue sarcomas.

An aspect of the invention is a prodrug represented by Formula I:

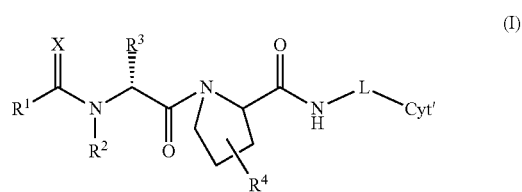

(I)

or a pharmaceutically acceptable salt thereof, wherein:

$R^1$ represents ($C_1$-$C_{10}$)alkyl, ($C_1$-$C_{10}$)alkoxy (e.g., tert-butyloxy), ($C_1$-$C_{10}$)alkyl-C(O)—($C_1$-$C_{10}$)alkyl, ($C_3$-$C_8$)cycloalkyl, ($C_3$-$C_8$)cycloalkyl($C_1$-$C_{10}$)alkyl, aryl, aryl($C_1$-$C_{10}$)alkyl, heteroaryl, or heteroaryl($C_1$-$C_{10}$)alkyl, wherein any $R^1$ is optionally substituted with one or more substituents independently selected from the group consisting of halo, hydroxy, carboxylate, cyano, amino, nitro, and thio (—SH); or —C(X)$R^1$ represents an N-terminally blocked alpha amino acid residue, wherein X is O;

$R^2$ represents H or a ($C_1$-$C_6$)alkyl;

$R^3$ represents H or a ($C_1$-$C_6$)alkyl;

$R^4$ is absent or represents a ($C_1$-$C_6$)alkyl, —OH, —NH$_2$, or halogen;

X represents O or S;

L represents a bond, or —N(H)-L- represents a self-immolative linker (e.g., —NH—(CH$_2$)$_4$—C(O)— or —NH—(CH$_2$)$_3$—C(O)—); and Cyt' represents a radical of an anthracycline or derivative thereof.

Anthracyclines and analogs thereof specifically include, without limitation, doxorubicin, daunorubicin, epirubicin, idarubicin, pirarubicin, valrubicin, aclarubicin, mitoxantrone, actinomycin, bleomycin, plicamycin, and mitomycin. For example, the anthracycline moiety can be represented by the formula

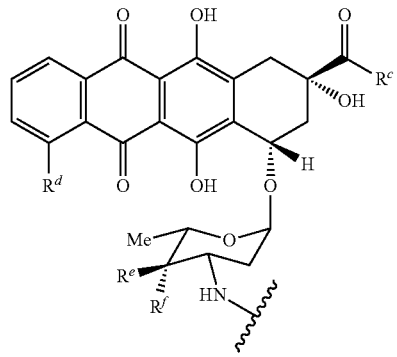

wherein,

R$^e$ represents (C$_1$-C$_6$)alkyl, (C$_1$-C$_6$)hydroxyalkyl, or (C$_1$-C$_6$)alkanoyloxy(C$_1$-C$_6$)alkyl, in particular methyl, hydroxymethyl, diethoxyacetoxymethyl, or butyryloxymethyl;

R$^d$ represents hydrogen, hydroxyl, or (C$_1$-C$_6$)alkoxy, in particular methoxy; one of R$^e$ and R$^f$ represents a hydrogen atom; and the other represents a hydrogen atom or a hydroxy or tetrahydropyrany-2-yloxy (OTHP) group.

In certain embodiments, Cyt' represents a radical of an anthracycline or analog thereof. In certain embodiments, Cyt' represents a radical of doxorubicin.

In certain embodiments, L represents a bond.

In an embodiment, L represents a bond, and Cyt' represents a radical of doxorubicin.

In certain embodiments, —N(H)-L- represents a self-immolative linker. For example, in one embodiment, the self-immolative linker is —NH—(CH$_2$)$_4$—C(O)—. In one embodiment, the self-immolative linker is —NH—(CH$_2$)$_3$—C(O)—.

In certain embodiments, the self-immolative linker is p-aminobenzyloxycarbonyl (PABC).

In certain embodiments, the self-immolative linker is 2,4-bis(hydroxymethyl)aniline.

In an embodiment, —N(H)-L- represents a self-immolative linker, and Cyt' represents a radical of doxorubicin.

In certain embodiments, R$^1$ represents (C$_1$-C$_{10}$)alkyl, optionally substituted with one or more substituents independently selected from the group consisting of halo, hydroxy, carboxylate, cyano, amino, nitro, and thio (—SH).

In certain embodiments, R$^1$ represents (C$_1$-C$_{10}$)alkoxy, optionally substituted with one or more substituents independently selected from the group consisting of halo, hydroxy, carboxylate, cyano, amino, nitro, and thio (—SH). For example, in certain embodiments, R$^1$ represents methoxy. As another example, in certain embodiments, R$^1$ represents tert-butyloxy.

In certain embodiments, R$^1$ represents (C$_1$-C$_{10}$)alkyl-C(O)—(C$_1$-C$_{10}$)alkyl, optionally substituted with one or more substituents independently selected from the group consisting of halo, hydroxy, carboxylate, cyano, amino, nitro, and thio (—SH).

In certain embodiments, R$^1$ represents (C$_3$-C$_8$)cycloalkyl, optionally substituted with one or more substituents independently selected from the group consisting of halo, hydroxy, carboxylate, cyano, amino, nitro, and thio (—SH). For example, in certain embodiments, R$^1$ represents cyclopropyl.

In certain embodiments, R$^1$ represents (C$_3$-C$_8$)cycloalkyl(C$_1$-C$_{10}$)alkyl, optionally substituted with one or more substituents independently selected from the group consisting of halo, hydroxy, carboxylate, cyano, amino, nitro, and thio (—SH).

In certain embodiments, R$^1$ represents aryl, optionally substituted with one or more substituents independently selected from the group consisting of halo, hydroxy, carboxylate, cyano, amino, nitro, and thio (—SH). For example, in certain embodiments, R$^1$ represents phenyl.

In certain embodiments, R$^1$ represents aryl(C$_1$-C$_{10}$)alkyl, optionally substituted with one or more substituents independently selected from the group consisting of halo, hydroxy, carboxylate, cyano, amino, nitro, and thio (—SH). For example, in certain embodiments, R$^1$ represents benzyl.

In certain embodiments, R$^1$ represents heteroaryl, optionally substituted with one or more substituents independently selected from the group consisting of halo, hydroxy, carboxylate, cyano, amino, nitro, and thio (—SH). In certain embodiments, R$^1$ represents an N-containing heteroaryl, optionally substituted with one or more substituents independently selected from the group consisting of halo, hydroxy, carboxylate, cyano, amino, nitro, and thio (—SH). In certain embodiments, R$^1$ represents an O-containing heteroaryl, optionally substituted with one or more substituents independently selected from the group consisting of halo, hydroxy, carboxylate, cyano, amino, nitro, and thio (—SH). In certain embodiments, R$^1$ represents an S-containing heteroaryl, optionally substituted with one or more substituents independently selected from the group consisting of halo, hydroxy, carboxylate, cyano, amino, nitro, and thio (—SH).

In certain embodiments, R$^1$ represents heteroaryl(C$_1$-C$_{10}$)alkyl, optionally substituted with one or more substituents independently selected from the group consisting of halo, hydroxy, carboxylate, cyano, amino, nitro, and thio (—SH). In certain embodiments, R$^1$ represents an N-containing heteroaryl(C$_1$-C$_{10}$)alkyl, optionally substituted with one or more substituents independently selected from the group consisting of halo, hydroxy, carboxylate, cyano, amino, nitro, and thio (—SH). In certain embodiments, R$^1$ represents an O-containing heteroaryl(C$_1$-C$_{10}$)alkyl, optionally substituted with one or more substituents independently selected from the group consisting of halo, hydroxy, carboxylate, cyano, amino, nitro, and thio (—SH). In certain embodiments, R$^1$ represents an S-containing heteroaryl(C$_1$-C$_{10}$)alkyl, optionally substituted with one or more substituents independently selected from the group consisting of halo, hydroxy, carboxylate, cyano, amino, nitro, and thio (—SH).

In certain embodiments, R$^1$ represents a radical of a cyclic aromatic moiety, preferably a mono-, bi-, or tri-cyclic including from 5-12 ring atoms, and is preferably a cyclic heteroaromatic including, for example, 1-4 nitrogen atoms, and even more preferably is a basic cyclic heteroaromatic moiety including at least one lone pair of electrons that is not part of the aromatic system (i.e., may extend in the plane of the ring), such as quinoline and isoquinoline, though may also be a heteroaromatic ring containing basic as well as non-basic nitrogen atoms, e.g., imidazole or purine.

In certain embodiments, R$^1$ represents quinolinyl.

In certain embodiments, R$^1$ represents isoquinolinyl.

In certain embodiments, —C(X)R$^1$ represents an N-terminally blocked alpha amino acid residue, wherein X is O.

In certain embodiments, R$^2$ represents H.

In certain other embodiments, R$^2$ represents a (C$_1$-C$_6$)alkyl. For example, in certain embodiments, R$^2$ represents methyl.

In certain embodiments, R$^3$ represents H.

In certain other embodiments, R$^3$ represents a (C$_1$-C$_6$)alkyl. For example, in certain embodiments, R$^3$ represents methyl, ethyl, propyl, or isopropyl. In certain embodiments, R$^3$ is methyl.

In certain embodiments, R$^4$ is absent.

In certain other embodiments, R$^4$ represents a (C$_1$-C$_6$)alkyl. For example, in certain embodiments, R$^4$ represents methyl.

In certain embodiments, R$^4$ represents —OH.

In certain embodiments, R$^4$ represents —NH$_2$.

In certain embodiments, R$^4$ represents halogen. For example, in certain embodiments, R$^4$ represents F. As another example, in certain embodiments, R$^4$ represents Cl.

In certain embodiments, X represents O.

In certain other embodiments, X represents S.

In certain embodiments, L is a bond, and the anthracycline or anthracycline derivative is selected from doxorubicin, daunorubicin, epirubicin, idarubicin, pirarubicin, aclarubicin, mitoxantrone, actinomycin, bleomycin, plicamycin, or mitomycin.

In certain embodiments, the anthracycline is doxorubicin.

In certain embodiments, —C(X)R$^1$ is a moiety which, at physiological pH, reduces cell permeability of the prodrug relative to the anthracycline or anthracycline derivative. For example, in various embodiments the cell permeability for the prodrug is less than: 10 percent, 20 percent, 30 percent, 40 percent, 50 percent, 60 percent, 70 percent, 75 percent, 80 percent, 85 percent, 90 percent, or 95 percent of the cell permeability for the anthracycline or anthracycline derivative. In certain embodiments the cell permeability for the prodrug is less than 50 percent of the cell permeability for the anthracycline or anthracycline derivative.

In certain embodiments, —C(X)R$^1$ comprises one or more functional groups that are ionized at physiological pH.

In certain embodiments, —C(X)R$^1$ is an acyl($C_1$-$C_{10}$) alkyl substituted with one or more functional groups that are ionized at physiological pH.

In certain embodiments, —C(X)R$^1$ is represented by the formula HO$_2$C—($C_1$-$C_{10}$)alkyl-C(O)—.

For example, in certain embodiments, —C(X)R$^1$ is represented by the formula HO$_2$C—(CH$_2$)$_2$—C(O)—.

In certain embodiments, —C(X)R$^1$ is selected from the group consisting of formyl, dansyl, acetyl, benzoyl, trifluoroacetyl, succinyl, and methoxysuccinyl.

In certain embodiments, —C(X)R$^1$ is formyl.
In certain embodiments, —C(X)R$^1$ is dansyl.
In certain embodiments, —C(X)R$^1$ is acetyl.
In certain embodiments, —C(X)R$^1$ is benzoyl.
In certain embodiments, —C(X)R$^1$ is trifluoroacetyl.
In certain embodiments, —C(X)R$^1$ is succinyl.
In certain embodiments, —C(X)R$^1$ is methoxysuccinyl.

In certain embodiments, —C(X)R$^1$ is selected from the group consisting of aryl($C_1$-$C_6$)acyl and heteroaryl($C_1$-$C_6$)acyl.

In certain embodiments, —C(X)R$^1$ is an aryl($C_1$-$C_6$)acyl.
In certain embodiments, —C(X)R$^1$ is a heteroaryl($C_1$-$C_6$)acyl.

In certain embodiments, the aryl($C_1$-$C_6$)acyl is a ($C_1$-$C_6$) acyl substituted with an aryl selected from the group consisting of benzyl, naphthalenyl, phenanthrenyl, phenolyl, and anilinyl.

In certain embodiments, the aryl($C_1$-$C_6$)acyl is a ($C_1$-$C_6$) acyl substituted with benzyl.
In certain embodiments, the aryl($C_1$-$C_6$)acyl is a ($C_1$-$C_6$) acyl substituted with naphthalenyl.
In certain embodiments, the aryl($C_1$-$C_6$)acyl is a ($C_1$-$C_6$) acyl substituted with phenanthrenyl.
In certain embodiments, the aryl($C_1$-$C_6$)acyl is a ($C_1$-$C_6$) acyl substituted with phenolyl.
In certain embodiments, the aryl($C_1$-$C_6$)acyl is a ($C_1$-$C_6$) acyl substituted with anilinyl.
In certain embodiments, the aryl($C_1$-$C_6$)acyl is a ($C_1$)acyl substituted with an aryl selected from the group consisting of benzyl, naphthalenyl, phenanthrenyl, phenolyl, and anilinyl.
In certain embodiments, the aryl($C_1$-$C_6$)acyl is a ($C_1$)acyl substituted with benzyl.
In certain embodiments, the aryl($C_1$-$C_6$)acyl is a ($C_1$)acyl substituted with naphthalenyl.
In certain embodiments, the aryl($C_1$-$C_6$)acyl is a ($C_1$)acyl substituted with phenanthrenyl.
In certain embodiments, the aryl($C_1$-$C_6$)acyl is a ($C_1$)acyl substituted with phenolyl.
In certain embodiments, the aryl($C_1$-$C_6$)acyl is a ($C_1$)acyl substituted with anilinyl.

In certain embodiments, —C(X)R$^1$ is a heteroaryl($C_1$-$C_6$) acyl.

In certain embodiments, the heteroaryl($C_1$-$C_6$)acyl is a ($C_1$-$C_6$)acyl substituted with a heteroaryl selected from the group consisting of pyrryl, furyl, thiophenyl (a/k/a thienyl), imidazolyl, oxazolyl, thiazolyl, triazolyl, pyrazolyl, pyridinyl, pyrazinyl, pyridazinyl, and pyrimidinyl.

In certain embodiments, the heteroaryl($C_1$-$C_6$)acyl is a ($C_1$-$C_6$)acyl substituted with pyrryl.
In certain embodiments, the heteroaryl($C_1$-$C_6$)acyl is a ($C_1$-$C_6$)acyl substituted with furyl.
In certain embodiments, the heteroaryl($C_1$-$C_6$)acyl is a ($C_1$-$C_6$)acyl substituted with thiophenyl (a/k/a thienyl).
In certain embodiments, the heteroaryl($C_1$-$C_6$)acyl is a ($C_1$-$C_6$)acyl substituted with imidazolyl.
In certain embodiments, the heteroaryl($C_1$-$C_6$)acyl is a ($C_1$-$C_6$)acyl substituted with oxazolyl.
In certain embodiments, the heteroaryl($C_1$-$C_6$)acyl is a ($C_1$-$C_6$)acyl substituted with thiazolyl.
In certain embodiments, the heteroaryl($C_1$-$C_6$)acyl is a ($C_1$-$C_6$)acyl substituted with triazolyl.
In certain embodiments, the heteroaryl($C_1$-$C_6$)acyl is a ($C_1$-$C_6$)acyl substituted with pyrazolyl.
In certain embodiments, the heteroaryl($C_1$-$C_6$)acyl is a ($C_1$-$C_6$)acyl substituted with pyridinyl.
In certain embodiments, the heteroaryl($C_1$-$C_6$)acyl is a ($C_1$-$C_6$)acyl substituted with pyrizinyl.
In certain embodiments, the heteroaryl($C_1$-$C_6$)acyl is a ($C_1$-$C_6$)acyl substituted with pyridazinyl.
In certain embodiments, the heteroaryl($C_1$-$C_6$)acyl is a ($C_1$-$C_6$)acyl substituted with pyrimidinyl.

In certain embodiments, the heteroaryl($C_1$-$C_6$)acyl is a ($C_1$)acyl substituted with a heteroaryl selected from the group consisting of pyrryl, furyl, thiophenyl (a/k/a thienyl), imidazolyl, oxazolyl, thiazolyl, triazolyl, pyrazolyl, pyridinyl, pyrazinyl, pyridazinyl, and pyrimidinyl.

In certain embodiments, the heteroaryl($C_1$-$C_6$)acyl is a ($C_1$)acyl substituted with pyrryl.
In certain embodiments, the heteroaryl($C_1$-$C_6$)acyl is a ($C_1$)acyl substituted with furyl.
In certain embodiments, the heteroaryl($C_1$-$C_6$)acyl is a ($C_1$)acyl substituted with thiophenyl (a/k/a thienyl).
In certain embodiments, the heteroaryl($C_1$-$C_6$)acyl is a ($C_1$)acyl substituted with imidazolyl.
In certain embodiments, the heteroaryl($C_1$-$C_6$)acyl is a ($C_1$)acyl substituted with oxazolyl.
In certain embodiments, the heteroaryl($C_1$-$C_6$)acyl is a ($C_1$)acyl substituted with thiazolyl.
In certain embodiments, the heteroaryl($C_1$-$C_6$)acyl is a ($C_1$)acyl substituted with triazolyl.
In certain embodiments, the heteroaryl($C_1$-$C_6$)acyl is a ($C_1$)acyl substituted with pyrazolyl.
In certain embodiments, the heteroaryl($C_1$-$C_6$)acyl is a ($C_1$)acyl substituted with pyridinyl.
In certain embodiments, the heteroaryl($C_1$-$C_6$)acyl is a ($C_1$)acyl substituted with pyrizinyl.
In certain embodiments, the heteroaryl($C_1$-$C_6$)acyl is a ($C_1$)acyl substituted with pyridazinyl.
In certain embodiments, the heteroaryl($C_1$-$C_6$)acyl is a ($C_1$)acyl substituted with pyrimidinyl.

In an embodiment, the prodrug is represented by a formula selected from the group consisting of:

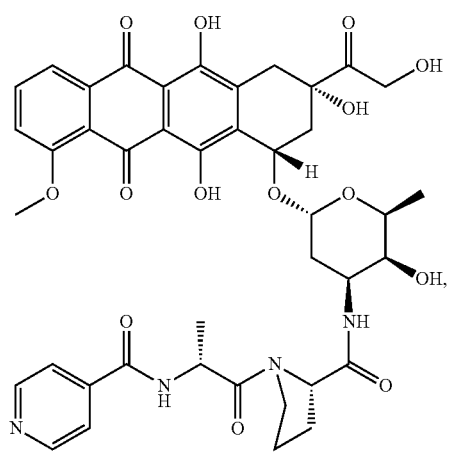

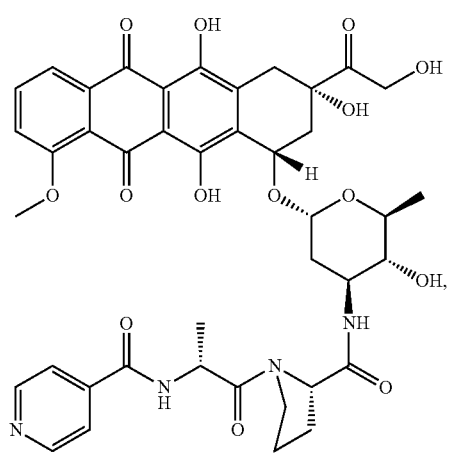

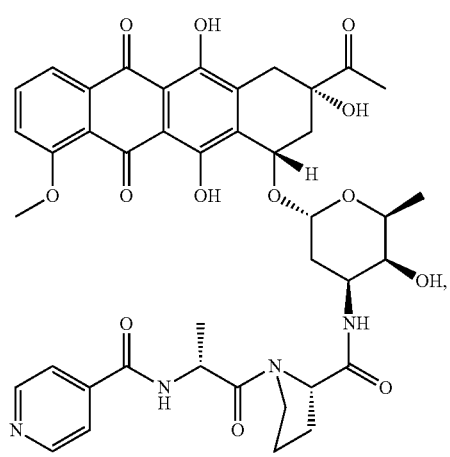

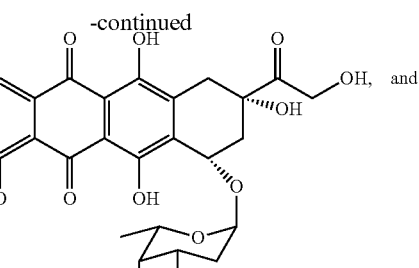

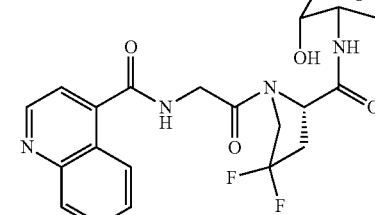

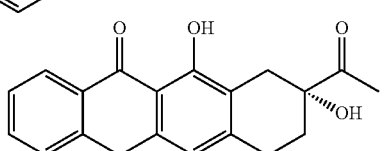

In an embodiment, the prodrug is represented by the formula

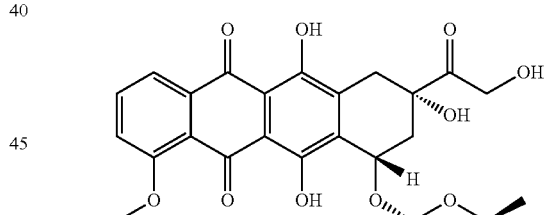

In an embodiment, the prodrug is N—((R)-1-((R)-2-(((2S,3S,4S,6R)-3-hydroxy-2-methyl-6-(((1S,3S)-3,5,12-trihydroxy-3-(2-hydroxyacetyl)-10-methoxy-6,11-dioxo-1,2,3,4,6,11-hexahydrotetracen-1-yl)oxy)tetrahydro-2H-pyran-4-yl)carbamoyl)pyrrolidin-1-yl)-1-oxopropan-2-yl) isonicotinamide, or a pharmaceutically acceptable salt thereof.

In an embodiment, the prodrug is N—((R)-1-((R)-2-(((2S,3R,4S,6R)-3-hydroxy-2-methyl-6-(((1S,3S)-3,5,12-trihydroxy-3-(2-hydroxyacetyl)-10-methoxy-6,11-dioxo-1,2,3,4,6,11-hexahydrotetracen-1-yl)oxy)tetrahydro-2H-pyran-4-yl)carbamoyl)pyrrolidin-1-yl)-1-oxopropan-2-yl)isonicotinamide, or a pharmaceutically acceptable salt thereof.

In an embodiment, the prodrug is N—((R)-1-((R)-2-(((2S,3S,4S,6R)-6-(((1S,3S)-3-acetyl-3,5,12-trihydroxy-10-methoxy-6,11-dioxo-1,2,3,4,6,11-hexahydrotetracen-1-yl)oxy)-3-hydroxy-2-methyltetrahydro-2H-pyran-4-yl)carbamoyl)pyrrolidin-1-yl)-1-oxopropan-2-yl)isonicotinamide, or a pharmaceutically acceptable salt thereof.

In an embodiment, the prodrug is N—((R)-1-((R)-2-(((2S,3S,4S,6R)-6-(((1S,3S)-3-acetyl-3,5,12-trihydroxy-6,11-dioxo-1,2,3,4,6,11-hexahydrotetracen-1-yl)oxy)-3-hydroxy-2-methyltetrahydro-2H-pyran-4-yl)carbamoyl)pyrrolidin-1-yl)-1-oxopropan-2-yl)isonicotinamide, or a pharmaceutically acceptable salt thereof.

An aspect of the invention is a pharmaceutical composition comprising a prodrug of the invention and a pharmaceutically acceptable carrier. In an embodiment, the pharmaceutical composition comprises two or more prodrugs of the invention.

An aspect of the invention is a method of making a pharmaceutical composition of the invention. The method includes the step of combining a compound of the invention with a pharmaceutically acceptable carrier. In an embodiment, the method further includes the step of formulating the pharmaceutical composition for a particular route of administration, for example, for oral administration or for intravenous administration.

An aspect of the invention relates to a packaged pharmaceutical, comprising a prodrug described herein formulated in a pharmaceutically acceptable excipient, in association with instructions (written and/or pictorial) describing the recommended dosage and/or administration of the formulation to a patient.

An aspect of the present invention relates to a method of treating a disorder characterized by fibroblast activation protein (FAP) upregulation, comprising administering to a subject in need thereof a therapeutically effective amount of a prodrug of the invention. Disorders characterized by FAP upregulation include, without limitation, cancer (e.g., solid tumors), abnormal cell proliferation, fibrosis, and inflammation. In an embodiment, the disorder characterized by FAP upregulation is selected from the group consisting of cancer, fibrosis, and inflammation.

In an embodiment, the disorder characterized by FAP upregulation is cancer (e.g., a solid tumor).

In an embodiment, the disorder characterized by FAP upregulation is a breast carcinoma.

In an embodiment, the disorder characterized by FAP upregulation is a non-small cell lung carcinoma.

In an embodiment, the disorder characterized by FAP upregulation is a colorectal carcinoma.

In an embodiment, the disorder characterized by FAP upregulation is fibrosis.

In an embodiment, the disorder characterized by FAP upregulation is inflammation.

In certain embodiments, the method of treating a disorder characterized by FAP upregulation further comprises administering to the subject in need thereof a therapeutically effective amount of a chemotherapeutic agent.

In certain embodiments, the method of treating a disorder characterized by FAP upregulation further comprises administering to the subject in need thereof a therapeutically effective amount of an anti-inflammatory agent.

An aspect of the present invention relates to a method of treating cancer, comprising administering to a subject in need thereof a therapeutically effective amount of a prodrug of the invention.

In an embodiment, the cancer is a breast carcinoma.

In an embodiment, the cancer is a non-small cell lung carcinoma.

In an embodiment, the cancer is a colorectal carcinoma.

In certain embodiments, the method of treating cancer further comprises administering to the subject in need thereof a therapeutically effective amount of a chemotherapeutic agent.

Definitions

In the context of this invention, a "drug" shall mean a chemical compound that may be administered to humans or animals as an aid in the treatment of disease. In particular, a drug is an active pharmaceutical agent.

As used herein, "physiological pH" means tissue or blood pH compatible with life. Physiological pH is typically 6.8 to 8.4. In one embodiment, physiological pH is 7.0 to 8.0. In one embodiment, physiological pH is 7.2 to 7.8.

The term "treat" or "treating" as used herein means prevent, slow or halt the progression of, reduce at least one symptom of, and/or eliminate a disease or condition of a subject. In one embodiment, "treat" or "treating" means slow or halt the progression of, reduce at least one symptom of, and/or eliminate a disease or condition of a subject.

The term "subject" as used herein refers to a living mammal. In an embodiment, a subject is a mouse, rat, hamster, guinea pig, rabbit, cat, dog, goat, sheep, pig, horse, cow, or non-human primate. In another embodiment, a subject is a human.

A "therapeutically effective amount" of a compound with respect to use in treatment, refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "self-eliminating linker" or "self-immolative linker" refers to a temporary extender, spacer, or placeholder unit attaching two or more molecules together by chemical bonds that are cleaved under defined conditions to release the two molecules. In general, a self-eliminating or self-immolative linker may be linear or branched, and may link two or more of the same molecules together, or may link two or more different molecules together. The self-eliminating or self-immolative linker may degrade, decompose, or fragment under, for example, physiological conditions, acidic conditions, basic conditions, or in the presence of specific chemical agents. Examples of self-eliminating linkers include, but are not limited to, p-aminobenzyloxycarbonyl (PABC) and 2,4-bis(hydroxymethyl)aniline.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal. In an embodiment, a prodrug has less than 10 percent activity relative to the free or active drug derived or released therefrom. In an embodiment, a prodrug has less than 5 percent activity relative to the free or active drug derived or released therefrom. In an embodiment, a prodrug has less than 1 percent activity relative to the free or active drug derived or released therefrom.

As used herein, a "prodrug of the invention" or a "compound of the invention" refers to any prodrug of Formula I as disclosed herein. Except if otherwise expressly excluded, the term "prodrug of the invention" or "compound of the invention" further encompasses pharmaceutically acceptable salts of such prodrug of Formula I.

The term "pharmaceutically acceptable salt" refers to any relatively non-toxic inorganic or organic acid addition salt of the prodrug(s). These salts can be prepared in situ during the final isolation and purification of the prodrug(s), or by separately reacting a purified prodrug(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. See, for example, Berge et al. (1977) "*Pharmaceutical Salts*", *J. Pharm. Sci.* 66:1-19.

In other cases, the compounds of the present invention may contain one or more acidic functional groups and, thus, are capable of forming pharmaceutically acceptable salts with pharmaceutically acceptable bases. The term "pharmaceutically acceptable salt" in these instances refers to any relatively non-toxic inorganic or organic base addition salts of the prodrug(s). These salts can likewise be prepared in situ during the final isolation and purification of the prodrug (s), or by separately reacting the purified prodrug(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "amino acid residue" or "amino acid" is intended to embrace all compounds, whether natural or synthetic, which include both an amino functionality and an acid functionality, including amino acid analogues and derivatives. In certain embodiments, the amino acids contemplated in the present invention are those naturally occurring amino acids found in proteins, or the naturally occurring anabolic or catabolic products of such amino acids, which contain amino and carboxyl groups.

Naturally occurring amino acids are identified throughout by the conventional three-letter and/or one-letter abbreviations, corresponding to the trivial name of the amino acid, in accordance with the following list. The abbreviations are accepted in the peptide art and are recommended by the IUPAC-IUB commission in biochemical nomenclature.

| Amino Acid | Three-letter | One-letter |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unknown or "other" | Xaa | X |

The term "amino acid residue" further includes analogues, derivatives, and congeners of any specific amino acid referred to herein, as well as C-terminal or N-terminal protected amino acid derivatives (e.g., modified with an N-terminal or C-terminal protecting group).

The term "peptide," as used herein, refers to a sequence of amino acid residues linked together by peptide bonds or by modified peptide bonds. The term "peptide" is intended to encompass peptide analogues, peptide derivatives, peptidomimetics and peptide variants. The term "peptide" is understood to include peptides of any length. Peptide sequences set out herein are written according to the generally accepted convention whereby the N-terminal amino acid is on the left, and the C-terminal amino acid is on the right.

The term "peptide analogue," as used herein, refers to a peptide comprising one or more non-naturally occurring amino acid. Examples of non-naturally occurring amino acids include, but are not limited to, D-amino acids (i.e., an amino acid of an opposite chirality to the naturally occurring form), N-α-methyl amino acids, C-α-methyl amino acids, β-methyl amino acids, 0-alanine (0-Ala), norvaline (Nva), norleucine (Nle), 4-aminobutyric acid (γ-Abu), 2-aminoisobutyric acid (Aib), 6-aminohexanoic acid (∈-Ahx), ornithine (orn), hydroxyproline (Hyp), sarcosine, citrulline, cysteic acid, cyclohexylalanine, α-amino isobutyric acid, t-butylglycine, t-butylalanine, 3-aminopropionic acid, 2,3-diaminopropionic acid (2,3-diaP), D- or L-phenylglycine, D- or L-2-naphthylalanine (2-Nal), 1,2,3,4-tetrahydroisoquinoline-3-carboxylic acid (Tic), D- or L-2-thienylalanine (Thi), D- or L-3-thienylalanine, D- or L-1-, 2-, 3- or 4-pyrenylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine, D- or L-p-methoxybiphenylalanine, methionine sulphoxide (MSO) and homoarginine (Har). Other examples include D- or L-2-indole(alkyl)alanines and D- or L-alkylalanines, wherein alkyl is substituted or unsubstituted methyl, ethyl, propyl, hexyl, butyl, pentyl, isopropyl, iso-butyl, or iso-pentyl, and phosphono- or sulfated (e.g., —SO$_3$H) non-carboxylate amino acids.

Other examples of non-naturally occurring amino acids include 3-(2-chlorophenyl)-alanine, 3-chloro-phenylalanine, 4-chloro-phenylalanine, 2-fluoro-phenylalanine, 3-fluoro-phenylalanine, 4-fluoro-phenylalanine, 2-bromo-phenylalanine, 3-bromo-phenylalanine, 4-bromo-phenylalanine, homophenylalanine, 2-methyl-phenylalanine, 3-methyl-phenylalanine, 4-methyl-phenylalanine, 2,4-dimethyl-phenylalanine, 2-nitro-phenylalanine, 3-nitro-phenylalanine, 4-nitro-phenylalanine, 2,4-dinitro-phenylalanine, 1,2,3,4-Tetrahydroisoquinoline-3-carboxylic acid, 1,2,3,4-tetrahydronorharman-3-carboxylic acid, 1-naphthylalanine, 2-naphthylalanine, pentafluorophenylalanine, 2,4-dichloro-phenylalanine, 3,4-dichloro-phenylalanine, 3,4-difluoro-phenylalanine, 3,5-difluoro-phenylalanine, 2,4,5-trifluoro-phenylalanine, 2-trifluoromethyl-phenylalanine, 3-trifluoromethyl-phenylalanine, 4-trifluoromethyl-phenylalanine, 2-cyano-phenyalanine, 3-cyano-phenyalanine, 4-cyano-phenyalanine, 2-iodo-phenyalanine, 3-iodo-phenyalanine, 4-iodo-phenyalanine, 4-methoxyphenylalanine, 2-aminomethyl-phenylalanine, 3-aminomethyl-phenylalanine, 4-aminomethyl-phenylalanine, 2-carbamoyl-phenylalanine, 3-carbamoyl-phenylalanine, 4-carbamoyl-phenylalanine, m-tyrosine, 4-amino-phenylalanine, styrylalanine, 2-amino-5-phenyl-pentanoic acid, 9-anthrylalanine, 4-tert-butyl-phenylalanine, 3,3-diphenyl-alanine, 4,4'-diphenylalanine, benzoylphenylalanine, α-methyl-phenylalanine, α-methyl-4-fluoro-phenylalanine, 4-thiazolylalanine, 3-benzothienylalanine, 2-thienylalanine, 2-(5-bromothienyl)-alanine, 3-thienylalanine, 2-furylalanine, 2-pyridylalanine, 3-pyridylalanine, 4-pyridylalanine, 2,3-diaminopropionic acid, 2,4-diaminobutyric acid, allylglycine, 2-amino-4-bromo-4-pentenoic acid, propargylglycine, 4-aminocyclopent-2-enecarboxylic acid, 3-aminocyclopentanecarboxylic acid, 7-amino-heptanoic acid, dipropylglycine, pipecolic acid, azetidine-3-carboxylic acid, cyclopropylglycine, cyclopropylalanine, 2-methoxy-phenylglycine, 2-thienylglycine, 3-thienylglycine, α-benzyl-proline, α-(2-fluoro-benzyl)-proline, α-(3-fluoro-benzyl)-proline, α-(4-fluoro-benzyl)-proline, α-(2-chloro-benzyl)-proline, α-(3-chloro-benzyl)-proline, α-(4-chloro-benzyl)-proline, α-(2-bromo-benzyl)-proline, α-(3-bromo-benzyl)-proline, α-(4-bromo-benzyl)-proline, α-phenethyl-proline, α-(2-methyl-benzyl)-proline, α-(3-methyl-benzyl)-proline, α-(4-methyl-benzyl)-proline, α-(2-nitro-benzyl)-proline, α-(3-nitro-benzyl)-proline, α-(4-nitro-benzyl)-proline, α-(1-naphthalenylmethyl)-proline, α-(2-naphthalenylmethyl)-proline, α-(2,4-dichloro-benzyl)-proline, α-(3,4-dichloro-benzyl)-proline, α-(3,4-difluoro-benzyl)-proline, α-(2-trifluoromethyl-benzyl)-proline, α-(3-trifluoromethyl-benzyl)-proline, α-(4-trifluoromethyl-benzyl)-proline, α-(2-cyano-benzyl)-proline, α-(3-cyano-benzyl)-proline, α-(4-cyano-benzyl)-proline, α-(2-iodo-benzyl)-proline, α-(3-iodo-benzyl)-proline, α-(4-iodo-benzyl)-proline, α-(3-phenyl-allyl)-proline, α-(3-phenyl-propyl)-proline, α-(4-tert-butyl-benzyl)-proline, α-benzhydryl-proline, α-(4-biphenylmethyl)-proline, α-(4-thiazolylmethyl)-proline, α-(3-benzo[b]thiophenylmethyl)-proline, α-(2-thiophenylmethyl)-proline, α-(5-bromo-2-thiophenylmethyl)-proline, α-(3-thiophenylmethyl)-proline, α-(2-furanylmethyl)-proline, α-(2-pyridinylmethyl)-proline, α-(3-pyridinylmethyl)-proline, α-(4-pyridinylmethyl)-proline, α-allyl-proline, α-propynyl-proline, γ-benzyl-proline, γ-(2-fluoro-benzyl)-proline, γ-(3-fluoro-benzyl)-proline, γ-(4-fluoro-benzyl)-proline, γ-(2-chloro-benzyl)-proline, γ-(3-chloro-benzyl)-proline, γ-(4-chloro-benzyl)-proline, γ-(2-bromo-benzyl)-proline, γ-(3-bromo-benzyl)-proline, γ-(4-bromo-benzyl)-proline, γ-(2-methyl-benzyl)-proline, γ-(3-methyl-benzyl)-proline, γ-(4-methyl-benzyl)-proline, γ-(2-nitro-benzyl)-proline, γ-(3-nitro-benzyl)-proline, γ-(4-nitro-benzyl)-proline, γ-(1-naphthalenylmethyl)-proline, γ-(2-naphthalenylmethyl)-proline, γ-(2,4-dichloro-benzyl)-proline, γ-(3,4-dichloro-benzyl)-proline, γ-(3,4-difluoro-benzyl)-proline, γ-(2-trifluoromethyl-benzyl)-proline, γ-(3-trifluoromethyl-benzyl)-proline, γ-(4-trifluoromethyl-benzyl)-proline, γ-(2-cyano-benzyl)-proline, γ-(3-cyano-benzyl)-proline, γ-(4-cyano-benzyl)-proline, γ-(2-iodo-benzyl)-proline, γ-(3-iodo-benzyl)-proline, γ-(4-iodo-benzyl)-proline, γ-(3-phenyl-allyl-benzyl)-proline, γ-(3-phenyl-propyl-benzyl)-proline, γ-(4-tert-butyl-benzyl)-proline, γ-benzhydryl-proline, γ-(4-biphenylmethyl)-proline, γ-(4-thiazolylmethyl)-proline, γ-(3-benzothioienylmethyl)-proline, γ-(2-thienylmethyl)-proline, γ-(3-thienylmethyl)-proline, γ-(2-furanylmethyl)-proline, γ-(2-pyridinylmethyl)-proline, γ-(3-pyridinylmethyl)-proline, γ-(4-pyridinylmethyl)-proline, γ-allyl-proline, γ-propynyl-proline, trans-4-phenyl-pyrrolidine-3-carboxylic acid, trans-4-(2-fluoro-phenyl)-pyrrolidine-3-carboxylic acid, trans-4-(3-fluoro-phenyl)-pyrrolidine-3-carboxylic acid, trans-4-(4-fluoro-phenyl)-pyrrolidine-3-carboxylic acid, trans-4-(2-chloro-phenyl)-pyrrolidine-3-carboxylic acid, trans-4-(3-chloro-phenyl)-pyrrolidine-3-carboxylic acid, trans-4-(4-chloro-phenyl)-pyrrolidine-3-carboxylic acid, trans-4-(2-bromo-phenyl)-pyrrolidine-3-carboxylic acid, trans-4-(3-bromo-phenyl)-pyrrolidine-3-carboxylic acid, trans-4-(4-bromo-phenyl)-pyrrolidine-3-carboxylic acid, trans-4-(2-methyl-phenyl)-pyrrolidine-3-carboxylic acid, trans-4-(3-methyl-phenyl)-pyrrolidine-3-carboxylic acid, trans-4-(4-methyl-phenyl)-pyrrolidine-3-carboxylic acid, trans-4-(2-nitro-phenyl)-pyrrolidine-3-carboxylic acid, trans-4-(3-nitro-phenyl)-pyrrolidine-3-carboxylic acid, trans-4-(4-nitro-phenyl)-pyrrolidine-3-carboxylic acid, trans-4-(1-naphthyl)-pyrrolidine-3-carboxylic acid, trans-4-

(2-naphthyl)-pyrrolidine-3-carboxylic acid, trans-4-(2,5-dichloro-phenyl)-pyrrolidine-3-carboxylic acid, trans-4-(2,3-dichloro-phenyl)-pyrrolidine-3-carboxylic acid, trans-4-(2-trifluoromethyl-phenyl)-pyrrolidine-3-carboxylic acid, trans-4-(3-trifluoromethyl-phenyl)-pyrrolidine-3-carboxylic acid, trans-4-(4-trifluoromethyl-phenyl)-pyrrolidine-3-carboxylic acid, trans-4-(2-cyano-phenyl)-pyrrolidine-3-carboxylic acid, trans-4-(3-cyano-phenyl)-pyrrolidine-3-carboxylic acid, trans-4-(4-cyano-phenyl)-pyrrolidine-3-carboxylic acid, trans-4-(2-methoxy-phenyl)-pyrrolidine-3-carboxylic acid, trans-4-(3-methoxy-phenyl)-pyrrolidine-3-carboxylic acid, trans-4-(4-methoxy-phenyl)-pyrrolidine-3-carboxylic acid, trans-4-(2-hydroxy-phenyl)-pyrrolidine-3-carboxylic acid, trans-4-(3-hydroxy-phenyl)-pyrrolidine-3-carboxylic acid, trans-4-(4-hydroxy-phenyl)-pyrrolidine-3-carboxylic acid, trans-4-(2,3-dimethoxy-phenyl)-pyrrolidine-3-carboxylic acid, trans-4-(3,4-dimethoxy-phenyl)-pyrrolidine-3-carboxylic acid, trans-4-(3,5-dimethoxy-phenyl)-pyrrolidine-3-carboxylic acid, trans-4-(2-pyridinyl)-pyrrolidine-3-carboxylic acid, trans-4-(3-pyridinyl)-pyrrolidine-3-carboxylic acid, trans-4-(6-methoxy-3-pyridinyl)-pyrrolidine-3-carboxylic acid, trans-4-(4-pyridinyl)-pyrrolidine-3-carboxylic acid, trans-4-(2-thienyl)-pyrrolidine-3-carboxylic acid, trans-4-(3-thienyl)-pyrrolidine-3-carboxylic acid, trans-4-(2-furanyl)-pyrrolidine-3-carboxylic acid, trans-4-isopropyl-pyrrolidine-3-carboxylic acid, 4-phosphonomethyl-phenylalanine, benzyl-phosphothreonine, (1'-amino-2-phenyl-ethyl)oxirane, (1'-amino-2-cyclohexyl-ethyl)oxirane, (1'-amino-2-[3-bromo-phenyl]ethyl)oxirane, (1'-amino-2-[4-(benzyloxy)phenyl]ethyl)oxirane, (1'-amino-2-[3,5-difluoro-phenyl]ethyl)oxirane, (1'-amino-2-[4-carbamoyl-phenyl]ethyl)oxirane, (1'-amino-2-[benzyloxy-ethyl])oxirane, (1'-amino-2-[4-nitro-phenyl]ethyl)oxirane, (1'-amino-3-phenyl-propyl)oxirane, (1'-amino-3-phenyl-propyl)oxirane, and/or salts and/or protecting group variants thereof.

The term "peptide derivative," as used herein, refers to a peptide comprising additional chemical or biochemical moieties not normally a part of a naturally occurring peptide. Peptide derivatives include peptides in which the amino-terminus and/or the carboxy-terminus and/or one or more amino acid side chain has been derivatised with a suitable chemical substituent group, as well as cyclic peptides, dual peptides, multimers of the peptides, peptides fused to other proteins or carriers, glycosylated peptides, phosphorylated peptides, peptides conjugated to lipophilic moieties (for example, caproyl, lauryl, stearoyl moieties) and peptides conjugated to an antibody or other biological ligand. Examples of chemical substituent groups that may be used to derivatise a peptide include, but are not limited to, alkyl, cycloalkyl and aryl groups; acyl groups, including alkanoyl and aroyl groups; esters; amides; halogens; hydroxyls; carbamyls, and the like. The substituent group may also be a blocking group such as Fmoc (fluorenylmethyl-O—CO—), carbobenzoxy (benzyl-O—CO—), monomethoxysuccinyl, naphthyl-NH—CO—, acetylamino-caproyl and adamantyl-NH—CO—. Other derivatives include C-terminal hydroxymethyl derivatives, O-modified derivatives (for example, C-terminal hydroxymethyl benzyl ether) and N-terminally modified derivatives including substituted amides such as alkylamides and hydrazides. The substituent group may be a "protecting group" as detailed herein.

The term "peptidomimetic," as used herein, refers to a compound that is structurally similar to a peptide and contains chemical moieties that mimic the function of the peptide. For example, if a peptide contains two charged chemical moieties having functional activity, a mimetic places two charged chemical moieties in a spatial orientation and constrained structure so that the charged chemical function is maintained in three-dimensional space. The term peptidomimetic thus is intended to include isosteres. The term "isostere," as used herein, refers to a chemical structure that can be substituted for a peptide because the steric conformation of the chemical structure is similar, for example, the structure fits a binding site specific for the peptide. Examples of peptidomimetics include peptides comprising one or more backbone modifications (i.e., amide bond mimetics), which are well known in the art. Examples of amide bond mimetics include, but are not limited to, —$CH_2NH$—, —$CH_2S$—, —$CH_2CH_2$—, —CH=CH— (cis and trans), —$COCH_2$—, —CH(OH)$CH_2$—, —$CH_2SO$—, —CS—NH— and —NH—CO— (i.e., a reversed peptide bond) (see, for example, Spatola, Vega Data Vol. 1, Issue 3, (1983); Spatola, in Chemistry and Biochemistry of Amino Acids Peptides and Proteins, Weinstein, ed., Marcel Dekker, New York, p. 267 (1983); Morley, J. S., Trends Pharm. Sci. pp. 463-468 (1980); Hudson et al., Int. J. Pept. Prot. Res. 14:177-185 (1979); Spatola et al., Life Sci. 38:1243-1249 (1986); Hann, J; Chem. Soc. Perkin Trans. 1, 307-314 (1982); Almquist et al., J Med Chem. 23:1392-1398 (1980); Jennings-White et al., Tetrahedron Lett. 23:2533 (1982); Szelke et al., EP 45665 (1982); Holladay et al., Tetrahedron Lett. 24:4401-4404 (1983); and Hruby, Life Sci. 31:189-199 (1982)). Other examples of peptidomimetics include peptides substituted with one or more benzodiazepine molecules (see, for example, James, G. L. et al. (1993) Science 260: 1937-1942) and peptides comprising backbones cross-linked to form lactams or other cyclic structures.

The term "variant peptide," as used herein, refers to a peptide in which one or more amino acid residue has been deleted, added or substituted in comparison to the amino acid sequence to which the peptide corresponds. Typically, when a variant contains one or more amino acid substitutions they are "conservative" substitutions. A conservative substitution involves the replacement of one amino acid residue by another residue having similar side chain properties. As is known in the art, the twenty naturally occurring amino acids can be grouped according to the physicochemical properties of their side chains. Suitable groupings include: alanine, valine, leucine, isoleucine, proline, methionine, phenylalanine and tryptophan (hydrophobic side chains); glycine, serine, threonine, cysteine, tyrosine, asparagine, and glutamine (polar, uncharged side chains); aspartic acid and glutamic acid (acidic side chains) and lysine, arginine and histidine (basic side chains). Another grouping of amino acids is phenylalanine, tryptophan, and tyrosine (aromatic side chains). A conservative substitution involves the substitution of an amino acid with another amino acid from the same group.

In certain embodiments, —C(X)$R^1$ represents an N-terminally blocked alpha amino acid residue, wherein X is O. An N-terminally blocked amino acid residue is an amino acid residue modified by the presence of a protecting group covalently linked to the amino group of said residue.

The phrase "protecting group" as used herein, means temporary substituents which protect a potentially reactive functional group from undesired chemical transformations.

The term "amino-protecting group" or "N-terminal protecting group" refers to those groups intended to protect the α-N-terminal of an amino acid or peptide or to otherwise protect the amino group of an amino acid or peptide against undesirable reactions during synthetic procedures. Commonly used N-protecting groups are disclosed in Greene,

*Protective Groups In Organic Synthesis*, (John Wiley & Sons, New York (1981)), which is hereby incorporated by reference. Additionally, protecting groups can be used as pro-drugs which are readily cleaved in vivo, for example, by enzymatic hydrolysis, to release the biologically active parent. α-N-protecting groups comprise lower alkanoyl groups such as formyl, acetyl ("Ac"), propionyl, pivaloyl, t-butylacetyl and the like; other acyl groups include 2-chloroacetyl, 2-bromoacetyl, trifluoroacetyl, trichloroacetyl, phthalyl, o-nitrophenoxyacetyl, -chlorobutyryl, benzoyl, 4-chlorobenzoyl, 4-bromobenzoyl, 4-nitrobenzoyl and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-ethoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyoxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; arylalkyl groups such as benzyl, triphenylmethyl, benzyloxymethyl, 9-fluorenylmethyloxycarbonyl (Fmoc) and the like and silyl groups such as trimethylsilyl and the like. Still other examples include theyl, succinyl, methoxysuccinyl, suberyl, adipyl, azelayl, dansyl, benzyloxycarbonyl, methoxyazelaly, methoxyadipyl, methoxysuberyl, and 2,4-dinitrophenyl.

The term "carboxy protecting group" or "C-terminal protecting group" refers to a carboxylic acid protecting ester or amide group employed to block or protect the carboxylic acid functionality while the reactions involving other functional sites of the compound are performed. Carboxy protecting groups are disclosed in Greene, *Protective Groups in Organic Synthesis* pp. 152-186 (1981), which is hereby incorporated by reference. Additionally, a carboxy protecting group can be used as a pro-drug whereby the carboxy protecting group can be readily cleaved in vivo, for example by enzymatic hydrolysis, to release the biologically active parent. Such carboxy protecting groups are well known to those skilled in the art, having been extensively used in the protection of carboxyl groups in the penicillin and cephalosporin fields as described in U.S. Pat. Nos. 3,840,556 and 3,719,667, the disclosures of which are hereby incorporated herein by reference. Representative carboxy protecting groups are $C_1$-$C_8$ lower alkyl (e.g., methyl, ethyl or t-butyl and the like); arylalkyl such as phenethyl or benzyl and substituted derivatives thereof such as alkoxybenzyl or nitrobenzyl groups and the like; arylalkenyl such as phenylethenyl and the like; aryl and substituted derivatives thereof such as 5-indanyl and the like; dialkylaminoalkyl such as dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl such as benzoyloxymethyl, benzoyloxyethyl and the like; arylalkylcarbonyloxyalkyl such as benzylcarbonyloxymethyl, 2-benzylcarbonyloxyethyl and the like; alkoxycarbonylalkyl or cycloalkyloxycarbonylalkyl such as methoxycarbonylmethyl, cyclohexyloxycarbonylmethyl, 1-methoxycarbonyl-1-ethyl and the like; alkoxycarbonyloxyalkyl or cycloalkyloxycarbonyloxyalkyl such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl such as 2-(phenoxycarbonyloxy)ethyl, 2-(5-indanyloxycarbonyloxy)ethyl and the like; alkoxyalkylcarbonyloxyalkyl such as 2-(1-methoxy-2-methylpropan-2-oyloxy)ethyl and like; arylalkyloxycarbonyloxyalkyl such as 2-(benzyloxycarbonyloxy)ethyl and the like; arylalkenyloxycarbonyloxyalkyl such as 2-(3-phenylpropen-2-yloxycarbonyloxy)ethyl and the like; alkoxycarbonylaminoalkyl such as t-butyloxycarbonylaminomethyl and the like; alkylaminocarbonylaminoalkyl such as methylaminocarbonylaminomethyl and the like; alkanoylaminoalkyl such as acetylaminomethyl and the like; heterocyclic carbonyloxyalkyl such as 4-methylpiperazinylcarbonyloxymethyl and the like; dialkylaminocarbonylalkyl such as dimethylaminocarbonylmethyl, diethylaminocarbonylmethyl and the like; (5-(lower alkyl)-2-oxo-1,3-dioxolen-4-yl)alkyl such as (5-t-butyl-2-oxo-1,3-dioxolen-4-yl)methyl and the like; and (5-phenyl-2-oxo-1,3-dioxolen-4-yl)alkyl such as (5-phenyl-2-oxo-1,3-dioxolen-4-yl)methyl and the like. Representative amide carboxy protecting groups are aminocarbonyl and lower alkylaminocarbonyl groups. For example, aspartic acid may be protected at the α-C-terminal by an acid labile group (e.g., t-butyl) and protected at the 3-C-terminal by a hydrogenation labile group (e.g., benzyl) then deprotected selectively during synthesis. As mentioned above, the protected carboxy group may also be a lower alkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester.

An "aliphatic chain" comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer.

"Cycloalkyl" means mono- or bicyclic or bridged saturated carbocyclic rings, each having from 3 to 12 carbon atoms. Likewise, preferred cycloalkyls have from 5-12 carbon atoms in their ring structure, and more preferably have 6-10 carbons in the ring structure.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywherein the moiety and can have either the (Z) or the (E) configuration about the double bond(s).

"Alkynyl" refers to hydrocarbyl moieties of the scope of alkenyl, but having one or more triple bonds in the moiety.

The term "alkylthio" refers to an alkyl group, as defined above, having a sulfur moiety attached thereto. In certain embodiments, the alkylthio moiety is represented by one of —(S)-alkyl, —(S)-alkenyl, —(S)-alkynyl, and —(S)—(CH$_2$)$_m$—R$^1$, wherein m and R$^1$ are defined below. Representative alkylthio groups include methylthio, ethylthio, and the like.

The terms "alkoxyl" or "alkoxy" as used herein refers to an alkyl group, as defined below, having an oxygen moiety attached thereto. Representative alkoxyl groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O— alkenyl, —O-alkynyl, —O—(CH$_2$)$_m$—R$^1$, where m and R$^1$ are described below.

The terms "amine" and "amino" are art-recognized and refer to both unsubstituted and substituted amines, e.g., a moiety that can be represented by the formulae:

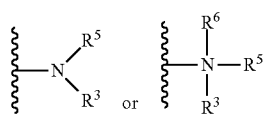

wherein R$^3$, R$^5$ and R$^6$ each independently represent a hydrogen, an alkyl, an alkenyl, —(CH$_2$)$_m$—R$^1$, or R$^3$ and R$^5$ taken together with the N atom to which they are attached complete a heterocycle having from 4 to 8 atoms in the ring structure; R$^1$ represents an alkenyl, aryl, cycloalkyl, a cycloalkenyl, a heterocyclyl, or a polycyclyl; and m is zero or an integer in the range of 1 to 8. In certain embodiments, only one of R$^3$ or R$^5$ can be a carbonyl, e.g., R$^3$, R$^5$, and the nitrogen together do not form an imide. In even more certain embodiments, R$^3$ and R$^5$ (and optionally R$^6$) each independently represent a hydrogen, an alkyl, an alkenyl, or —(CH$_2$)$_m$—R$^1$. Thus, the term "alkylamine" as used herein means an amine group, as defined above, having a substituted or unsubstituted alkyl attached thereto, i.e., at least one of R$_3$ and R$_5$ is an alkyl group. In certain embodiments, an amino group or an alkylamine is basic, meaning it has a conjugate acid with a pK$_a$≥7.00, i.e., the protonated forms of these functional groups have pK$_a$s relative to water above about 7.00.

The term "aryl" as used herein includes 5- to 12-membered substituted or unsubstituted single-ring and polycyclic aromatic groups in which each atom of the ring is carbon (i.e., carbocyclic aryl). Preferably, aryl groups include 5- to 12-membered rings, more preferably 6- to 10-membered rings. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, and/or heterocyclyls. Carbocyclic aryl groups include benzene, naphthalene, anthracene, phenanthrene, phenol, aniline, and the like.

The term "heteroaryl" as used herein includes 5- to 12-membered substituted or unsubstituted single-ring and polycyclic aromatic groups in which one or more atoms of the aromatic ring or ring system are heteroatoms. Preferably, heteroaryl groups include 5- to 12-membered rings, more preferably 6- to 10-membered rings. The term "heteroaryl" also includes polycyclic ring systems having two or more cyclic rings in which two or more atoms are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include substituted or unsubstituted aromatic 5- to 12-membered ring structures, more preferably 6- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine, pyrimidine, purine, quinoline, isoquinoline, carbazole, and the like.

The term "heterocyclyl" or "heterocyclic group" refer to 3- to 12-membered ring structures, more preferably 5- to 12-membered rings, more preferably 6- to 10-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —CF$_3$, —CN, and the like.

The term "carbonyl" is art-recognized and includes such moieties as can be represented by the formula:

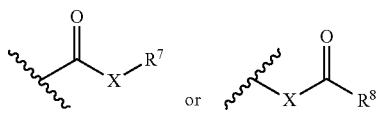

wherein X is a bond or represents an oxygen or a sulfur, and $R^7$ represents a hydrogen, an alkyl, an alkenyl, —$(CH_2)_m$—$R^1$ or a pharmaceutically acceptable salt, $R^8$ represents a hydrogen, an alkyl, an alkenyl or —$(CH_2)_m$—$R^1$, where m and $R^1$ are as defined above. Where X is an oxygen and $R^7$ or $R^8$ is not hydrogen, the formula represents an "ester." Where X is an oxygen, and $R^7$ is as defined above, the moiety is referred to herein as a carboxyl group, and particularly when $R^7$ is a hydrogen, the formula represents a "carboxylic acid". Where X is an oxygen, and $R^8$ is a hydrogen, the formula represents a "formate." In general, where the oxygen atom of the above formula is replaced by a sulfur, the formula represents a "thiocarbonyl" group. Where X is a sulfur and $R^7$ or $R^8$ is not hydrogen, the formula represents a "thioester" group. Where X is a sulfur and $R^7$ is a hydrogen, the formula represents a "thiocarboxylic acid" group. Where X is a sulfur and $R^8$ is a hydrogen, the formula represents a "thioformate" group. On the other hand, where X is a bond, and $R^7$ is not hydrogen, the above formula represents a "ketone" group. Where X is a bond, and $R^7$ is a hydrogen, the above formula represents an "aldehyde" group.

The term "thioxamide," as used herein, refers to a moiety that can be represented by the formula:

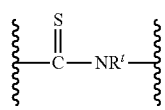

in which $R^t$ is selected from the group consisting of the group consisting of hydrogen, alkyl, cycloalkyl, aralkyl, or aryl, preferably hydrogen or alkyl. Moreover, "thioxamide-derived" compounds or "thioxamide analogues" refer to compounds in which one or more amide groups have been replaced by one or more corresponding thioxamide groups. Thioxamides are also referred to in the art as "thioamides."

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "nitro" means —$NO_2$; the term "halogen" designates —F, —Cl, —Br, or —I; the term "sulfhydryl" means —SH; the term "hydroxyl" means —OH; the term "sulfonyl" means —$SO_2$—; the term "azido" means —$N_3$; the term "cyano" means —CN; the term "isocyanato" means —NCO; the term "thiocyanato" means —SCN; the term "isothiocyanato" means —NCS; and the term "cyanato" means —OCN.

The term "sulfamoyl" is art-recognized and includes a moiety that can be represented by the formula:

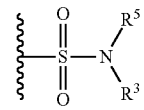

in which $R^3$ and $R^5$ are as defined above.

The term "sulfate" is art recognized and includes a moiety that can be represented by the formula:

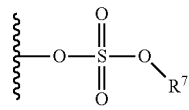

in which $R^7$ is as defined above.

The term "sulfonamide" is art recognized and includes a moiety that can be represented by the formula:

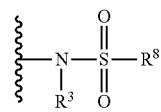

in which $R^3$ and $R^8$ are as defined above.

The term "sulfonate" is art-recognized and includes a moiety that can be represented by the formula:

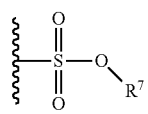

in which $R^7$ is an electron pair, hydrogen, alkyl, cycloalkyl, or aryl.

The terms "sulfoxido" or "sulfinyl", as used herein, refers to a moiety that can be represented by the formula:

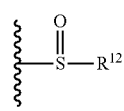

in which $R^{12}$ is selected from the group consisting of the group consisting of hydrogen, alkyl, alkenyl, alkynyl, cycloalkyl, heterocyclyl, aralkyl, or aryl.

As used herein, the definition of each expression, e.g., alkyl, m, n, etc., when it occurs more than once in any structure, is intended to be independent of its definition elsewhere in the same structure.

For purposes of this invention, the chemical elements are identified in accordance with the Periodic Table of the Elements, CAS version, *Handbook of Chemistry and Physics,* 67th ed., 1986-87, inside cover.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis or by derivation with a chiral auxiliary, where the resulting diastereomeric mixture is separated and the auxiliary group cleaved to provide the pure desired enantiomer. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomer.

Conjoint Therapy

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with a compound of the invention when the administration of the other therapeutic agents is temporally separated from the administration of the compound of the invention. The separation in time between the administration of these compounds may be a matter of minutes or it may be longer.

The compounds of the invention may also be administered in conjunction with an anti-cancer therapy. Anti-cancer therapies include cancer medicaments, radiation, and surgical procedures. As used herein, a "cancer medicament" refers to an agent which is administered to a subject for the purpose of treating a cancer. As used herein, "treating a cancer" includes preventing the development of a cancer, reducing the symptoms of cancer, and/or inhibiting the growth of an established cancer. In one embodiment, "treating a cancer" means reducing the symptoms of cancer and/or inhibiting the growth of an established cancer, whether at a primary site or metastatic. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

A chemotherapeutic agent can be selected from the group consisting of methotrexate, vincristine, adriamycin, cisplatin, carboplatin, non-sugar containing chloroethylnitrosoureas, 5-fluorouracil, mitomycin C, bleomycin, doxorubicin, dacarbazine, taxol, fragyline, Meglamine GLA, valrubicin, carmustine and poliferposan, MMI270, BAY 12-9566, RAS famesyl transferase inhibitor, famesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/ strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/ oral paclitaxel, Oral Taxoid, SPU-077/Cisplatin, HMR 1275/Flavopiridol, CP-358 (774)/EGFR, CP-609 (754)/ RAS oncogene inhibitor, BMS-182751/oral platinum, UFT (Tegafur/Uracil), Ergamisol/Levamisole, Eniluracil/ $776C_{85/5}$ FU enhancer, Campto/Levamisole, Camptosar/ Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/ Epirubicin, DepoCyt, ZD1839, LU 79553/Bis-Naphthalimide, LU 103793/Dolastain, Caetyx/liposomal doxorubicin, Gemzar/Gemcitabine, ZD 0473/Anormed, YM 116, iodine seeds, CDK4 and CDK2 inhibitors, PARP inhibitors, D4809/Dexifosamide, Ifes/Mesnex/Ifosamide, Vumon/ Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'- DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bisguanylhydrazone; MGBG), Pentostatin (2'deoxycoformycin), Semustine (methyl-CCNU), Teniposide (VM-26) and Vindesine sulfate, but it is not so limited.

An immunotherapeutic agent may be selected from the group consisting of Ributaxin, Herceptin, Quadramet, Panorex, IDEC-Y2B8, BEC2, $C_{225}$, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA, but it is not so limited.

A cancer vaccine may be selected from the group consisting of EGF, anti-idiotypic cancer vaccines, gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vaccine, TA-HPV, TA-CIN, DISC-virus and ImmuCyst/TheraCys, but it is not so limited.

The compounds of the invention may also be administered in conjunction with an anti-inflammatory agent. Anti-inflammatory agents include nonsteroidal anti-inflammatory drugs (NSAIDs), elemental gold, adrenocorticosteroids, vitamin D, vitamin E, and statins (HMG-Co-A reductase inhibitors). NSAIDs include, without limitation, aspirin, choline salicylate, celecoxib, diclofenac potassium, diclofenac sodium, diflunisal, etodolac, fenoprofen calcium, flurbiprofen, ibuprofen, indomethacin, ketoprofen, magnesium salicylate, meclofenamate sodium, mefenamic acid, meloxicam, nabumetone, naproxen, naproxen sodium, oxaprozin, piroxicam, rofecoxib, salsalate, sodium salicylate, sulindac, tolmetin sodium, and valdecoxib. Adrenocorticosteroids include, without limitation, betamethasone, cortisol (hydrocortisone), cortisone, dexamethasone, fludrocortisone, fluticasone, methylprednisolone, paramethasone, prednisolone, prednisone, tetrahydrocortisol, and triamcinolone. Statins include, without limitation, atorvastatin, cerivastatin, fluvastatin, lovastatin, pitavastatin, pravastatin, rosuvastatin, and simvastatin.

Dosages & Dosing Regimens

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for oral administration than for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

Generally, daily intravenous doses of active compound or compounds will be from about 0.001 milligrams/kg per day to 100 milligrams/kg per day. It is expected that intravenous doses in the range of 0.05 to 5 milligrams/kg, in one or several administrations per day, will yield the desired results. Intravenous dosing on other schedules is also contemplated by the invention, e.g., every-other day, semi-weekly, weekly, biweekly, and monthly. Similar dosing for other parenteral routes of administration is also contemplated by the invention.

Generally, daily oral doses of active compound or compounds will be from about 0.01 milligrams/kg per day to 1000 milligrams/kg per day. It is expected that oral doses in the range of 0.5 to 50 milligrams/kg, in one or several administrations per day, will yield the desired results. Oral dosing on other schedules is also contemplated by the invention, e.g., every-other day, semi-weekly, weekly, biweekly, and monthly.

Dosage may be adjusted appropriately to achieve desired drug levels, local or systemic, depending upon the mode of administration. For example, it is expected that intravenous administration would be from an order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

Pharmaceutical Formulations & Modes of Administration

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, intravenous, intramuscular, intraperitoneal, subcutaneous, direct injection (for example, into a tumor), mucosal, inhalation, and topical.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) ($\alpha$1-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, *Keystone, Colorado*, March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (m), most preferably 0.5 to 5 m, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically-acceptable carrier. The term "pharmaceutically-acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

Having now described the present invention in detail, the same will be more clearly understood by reference to the following examples, which are included herewith for purposes of illustration only and are not intended to be limiting of the invention.

EXAMPLES

Example 1

Synthesis of 3099DOX

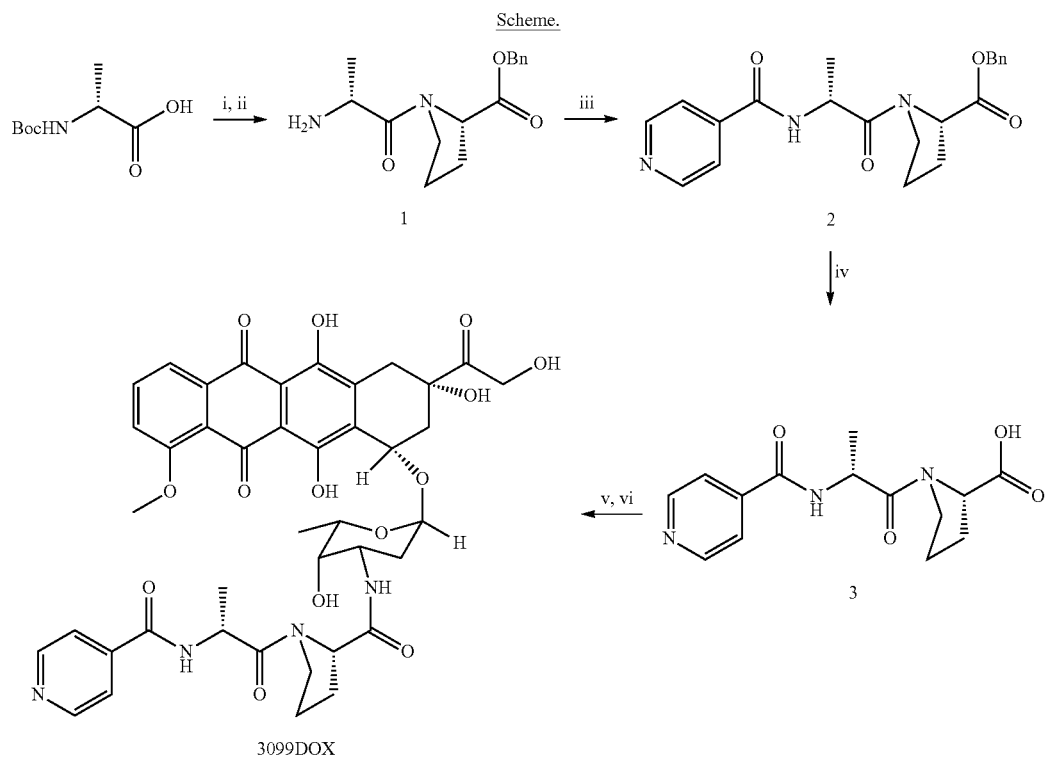

3099DOX

Reagents and conditions: i. H-Pro-OBzl, EDCI, HOBt, DIEA; ii. 4N HCl in dioxane, 92% over two steps; iii. Isonicotinoyl chloride, DIEA, 86%; iv. H$_2$/Pd—C, 93%; v. EDCI, HOSu; vi. Doxorubicin.HCl, phosphate buffer, DMSO, 81% over two steps.

Synthesis of Compound 1

EDCI.HCl (2.9 g, 15 mmol), HOBt (1.6 g, 12 mmol) and DIEA (2.0 mL, 11.5 mmol) were added to a solution of N-Boc-D-Ala-OH (1.9 g, 10 mmol) in anhydrous DMF (40 mL) under ice-water bath cooling. The resulting mixture was stirred at room temperature for 20 min, cooled down again with ice-water bath and L-proline benzyl ester hydrochloride (2.54 g, 10.5 mmol) was added followed by another 2.0 mL of DIEA. The reaction mixture was stirred at room temperature overnight and then condensed in vacuo. The residue was dissolved with ethyl acetate (150 mL), washed sequentially by 0.1 N KHSO$_4$ (3×40 mL), aq. NaHCO$_3$ (3×40 mL), brine (30 mL). The organic phase was dried over anhydrous MgSO$_4$, filtered, and evaporated in vacuo to give N-Boc-D-Ala-L-Pro-OBzl which was then added to a solution of 4 N HCl in dioxane (30 mL) under ice-water cooling. The resulting mixture was stirred at room temperature for 2 hrs and then condensed in vacuo. The residue was co-evaporated with dichloromethane (3×30 mL) in vacuo to completely dry. Compound 1 was thus obtained as a white powder (2.9 g, 92% over two steps).

Synthesis of Compound 2

A solution of compound 1 (2.8 g, 8.9 mmol) in anhydrous dichloromethane (100 mL) was stirred under ice-water bath cooling. DIEA (4.6 mL, 27 mmol) was then added slowly followed by the addition of isonicotinoyl chloride hydrochloride (1.75 g, 9.8 mmol) portion-wise over 10 min. The resulting mixture was stirred at room temperature for 5 hrs until the reaction was complete, then diluted with more dichloromethane (100 mL), washed by water (20 mL), aq. NaHCO$_3$ (2×20 mL), aq. NaCl (20 mL), dried over anhydrous MgSO$_4$, filtered, evaporated in vacuo to give crude compound 2 which was further purified with silica gel flash column chromatography (CH$_2$Cl$_2$:MeOH, 20:1) to afford the pure product 2 (2.9 g, 86%).

Synthesis of Compound 3

Compound 2 (1.5 g, 3.9 mmol) was added to a suspension solution of 10% Pd—C (0.15 g) in methanol (20 mL). The mixture was degassed under reduced pressure and placed under H$_2$ (50 psi). The mixture was stirred at room temperature for 3 hrs until the reaction was complete. The catalyst was then removed by filtration through Celite. The filtrate was concentrated in vacuo to complete dryness to give compound 3 as a white powder (1.05 g, 93%).

Synthesis of 3099DOX

EDCI.HCl (785 mg, 3.15 mmol) and N-hydroxysuccinimide (0.38 g, 3.3 mmol) were added to a solution of compound 3 (0.87 g, 3.0 mmol) in anhydrous DMF (25 mL) under ice-water bath cooling. The reaction mixture was stirred at room temperature for 3 hrs, concentrated in vacuo, re-dissolved into DMSO (10 mL) to make Solution A.

A pH 7.8 phosphate buffer (50 mL) was added slowly to another solution of Doxorubicin HCl (1.9 g, 3.3 mmol) in DMSO (140 mL) with good stirring under ice-water bath cooling. Solution A was then added and the resulting mixture was stirred at room temperature for 8 hrs, cooled down again with ice-water bath, diluted with water (80 mL) and dichloromethane (800 mL). The organic phase was partitioned and separated, washed by aq. NaCl (2×200 mL), dried over anhydrous $Na_2SO_4$, concentrated and purified with silica gel flash column chromatography ($CH_2Cl_2$:MeOH, 20:1 to 7:1) to give the pure compound 3099DOX as a little sticky dark-red powder which was re-dissolved with 2:3 of acetontrile-water and lyophilized to produce a good light red powder (2.0 g, 81% over two steps).

Analysis (i) LCMS of compound 3099DOX.
0-3 min: 2% B; 3-20 min: 2-98% B; 20-25 min: 98% B.
Ran with 1.8 μm particle size column on the Old LCMS.
Calc. MW, 816; the peak at 13.5 min was observed, 839.2:[M+Na], 403.2.
(ii)$^1$H NMR ($D_2O$/ACN-$d_3$, 1:1) showed a 2:8 of two rotamers.
(iii)$^1$H NMR ($CDCl_3$) showed a single rotamer.
(iv) Purity Analysis
HPLC Conditions:
Column: Agilent Eclipsc Plus C18, 4.6×50 mm, 1.8 m particle size
Column Temp: 27±2° C.
Sample Temp: ambient
Flow Rate: 0.5 mL/min
UV Detection Wavelength: 254 nm
Mobile Phase: A: 0.10% $CF_3COOH$ in water
B: 0.08% $CF_3COOH$ in acetonitrile
Gradient Pump Program:

| Step Time (minutes) | Elapsed Time (minutes) | % A (Aqueous) | % B (Organic) |
|---|---|---|---|
| 0 | 0 | 98 | 2 |
| 3 | 3 | 98 | 2 |
| 17 | 20 | 2 | 98 |
| 5 | 25 | 2 | 98 |

The column equilibrated with the initial composition mobile phase prior to commencing the analysis.
Retention time: 13.48 min; Purity: 99.39% (TAN).
(v) Stability Tests of 3099DOX (solid powder, open vials)

| | Remaining Purity % | | | | |
|---|---|---|---|---|---|
| Test Conditions | Day 0 | 1 week | 1 month | 2 month | 3 month |
| 22° C./72% RH | 99.4 | 99.3 | 99.5 | 98.1 | 97.5 |
| 40° C./75% RH | 99.4 | 99.3 | 98.8 | 96.3 | 95.3 |

Example 2

Doxorubicin Prodrugs

| Compound | Structures | Bioassay |
|---|---|---|
| 3099DOX | [structure of 3099DOX] | CellTiter-Glo cell viability assay with IM-9 cells<br>EC50 (prodrug alone) = 190 μM<br>EC50 (prodrug + 50 nM FAP) = 430 nM<br>EC50 (prodrug + 50 nM PREP) = 110 μM |

-continued

| Compound | Structures | Bioassay |
| --- | --- | --- |
| z-GP-DOX | 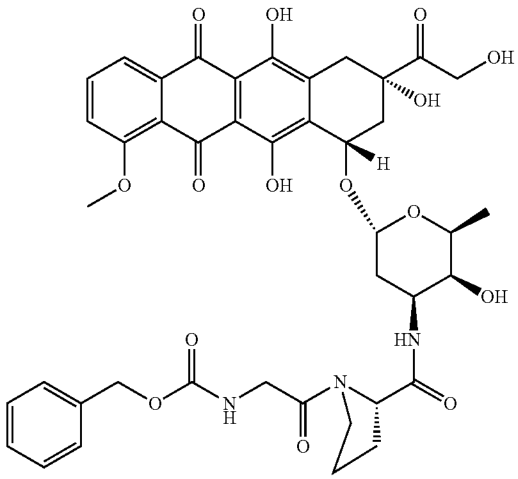 | |
| 3996DOX | 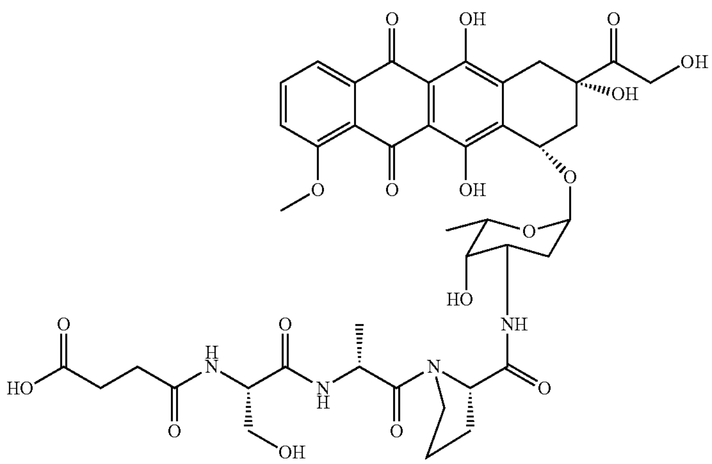 | CellTiter-Blue cell viability assay with CT26 cells<br>EC50 (prodrug alone) = 190 μM<br>EC50 (prodrug + 50 nM FAP) = 26 μM<br>EC50 (prodrug + 50 nM PREP) = 210 μM |

Example 3

Enzyme Kinetics of 3099DOX Activation by FAP

Michaelis-Menten enzyme kinetics for FAP were measured using a SpectraMax M2e microplate reader (Molecular Devices, Sunnyvale, CA, USA). The assays were performed in FAP buffer (50 mM Tris, 140 mM NaCl, pH 7.5) at 25° C., and the fluorescence continuously monitored at excitation and emission wavelengths of 380 and 460 nm, respectively. Kinetic constants ($k_{cat}$ and $K_m$) were determined using GP-AMC (Bachem, Torrance, CA, USA), Ac-(D)-AP-AFC (MP Biomedicals, Solon, OH, USA) and test article concentrations equivalent to 0.1-5 times their respective $K_m$ values, and with 5-10 nM enzyme. All assays were performed in triplicate, and the results were calculated with a nonlinear regression analysis, relying on a Michaelis-Menten curve fit using GraphPad software.

Figure 2:
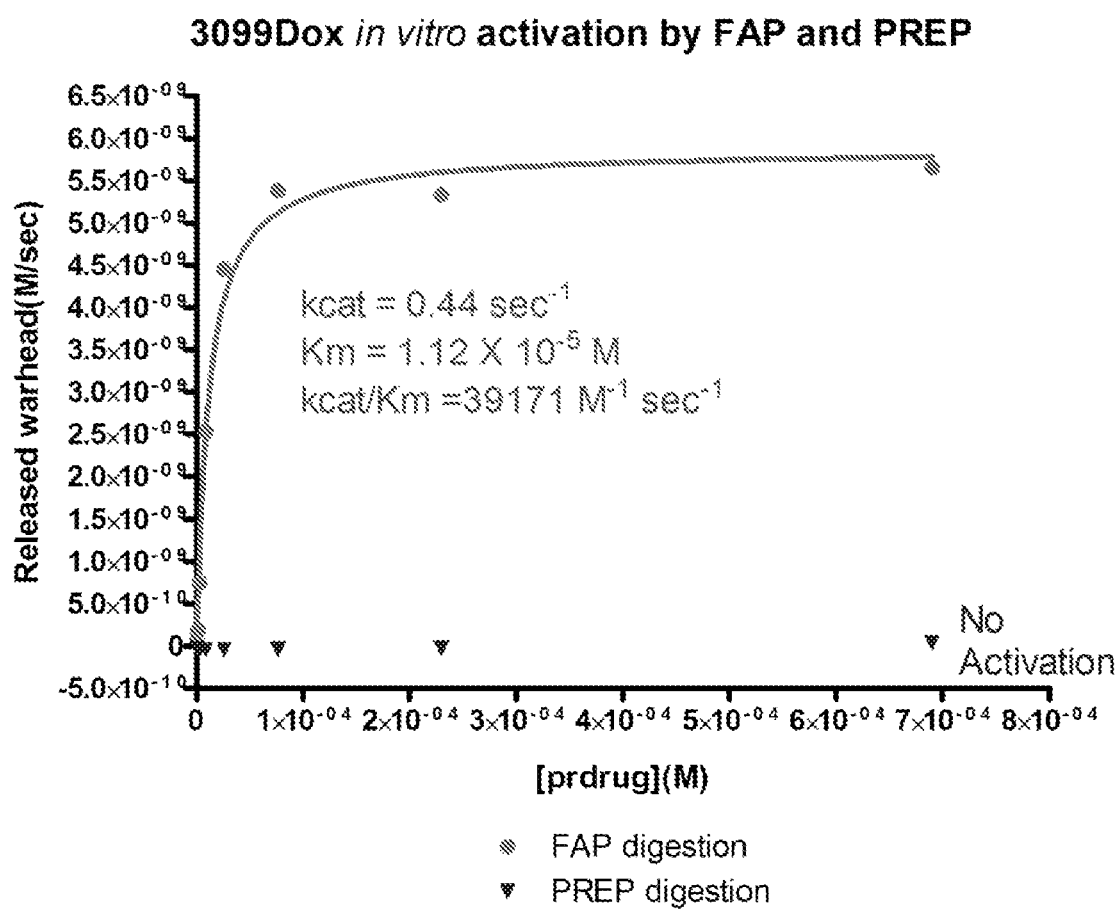
FIG. 2 is a graph depicting in vitro enzyme kinetics of 3099DOX activation by FAP and PREP.

3099DOX at various concentrations ranging from $8.5 \times 10^{-6}$ M to $6.9 \times 10^{-4}$ M was incubated with $1.34 \times 10^{-8}$ M FAP or PREP at 37° C., and released doxorubicin measured. Results of kinetic analysis are shown in FIG. 2. While 3099DOX had essentially no activation with PREP, 3099DOX was activated by FAP with $V_{max}=5.877 \times 10^{-9}$ M/sec, $K_m=1.12 \times 10^{-5}$ M, $k_{cat}$ ($V_{max}/[E]$)=0.44 sec$^{-1}$, and $k_{cat}/K_m=39171$ M$^{-1}$sec$^{-1}$.

Example 4

Rate of Recombinant FAP Activity on Doxorubicin Prodrugs

Figure 3:
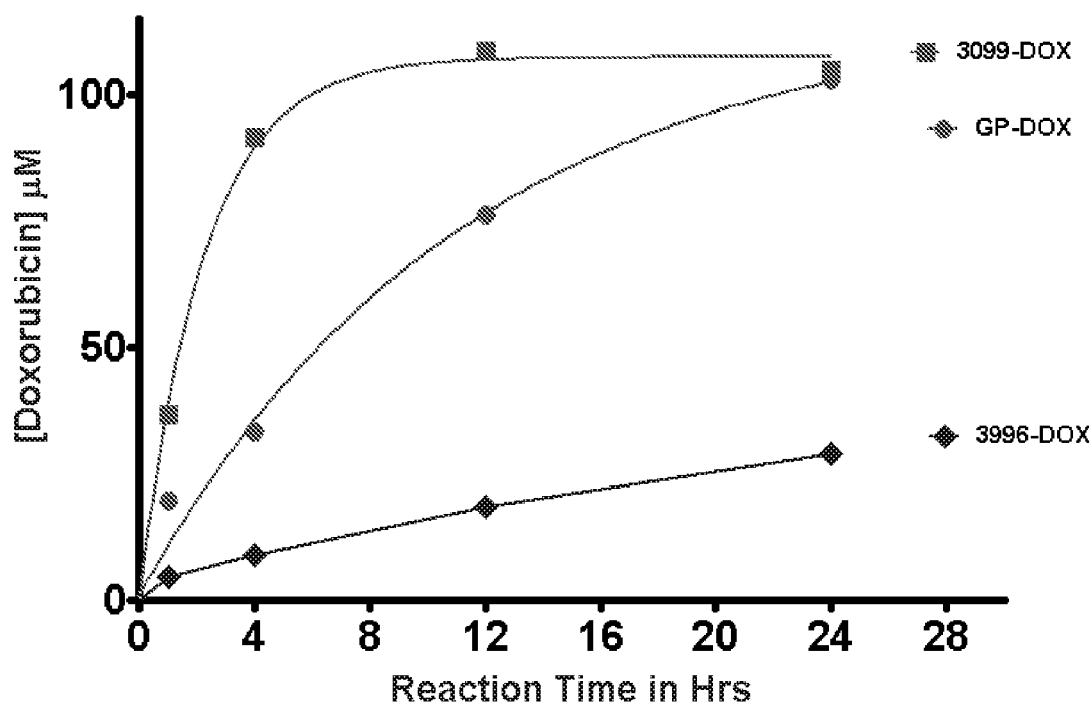
FIG. 3 is a graph depicting rate of recombinant FAP activity on doxorubicin prodrugs. GP-DOX refers to z-GP-DOX.

3099DOX, z-GP-DOX, and 3996DOX were incubated in the presence of recombinant FAP at 37° C. for 24 hours. Released doxorubicin was measured at 1, 4, 12, and 24 hours. Results are shown in FIG. 3. 3099DOX yielded free doxorubicin significantly faster than either z-GP-DOX or 3996DOX, reaching maximum in approximately 8 h.

Example 5

Specificity of 3099DOX Activation by FAP

Figure 4:
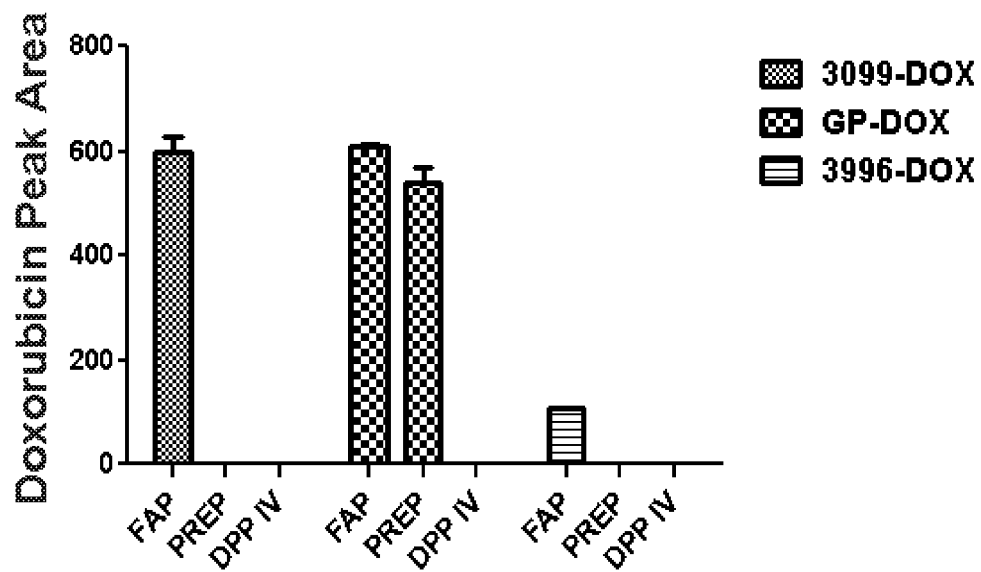
FIG. 4 is a bar graph depicting specificity of 3099DOX activation by FAP.

Doxorubicin prodrugs 3099DOX, z-GP-DOX, and 3996DOX, each at 100 μM, were digested 5 mg/mL FAP, PREP, or dipeptidyl peptidase IV (DPP IV) for 24 hours at 37° C. Total doxorubicin was measured for each assay. Results are shown in FIG. 4. Doxorubicin was released from 3099DOX by FAP but neither PREP nor DPP IV. A similar amount of doxorubicin was released from z-GP-DOX by FAP and PREP, but essentially none by DPP IV. Only about 15 percent as much doxorubicin was released from 3996DOX by FAP, but essentially none by PREP or DPP IV.

Example 6

Activation of 3099DOX in Mouse Plasma

Figure 5:
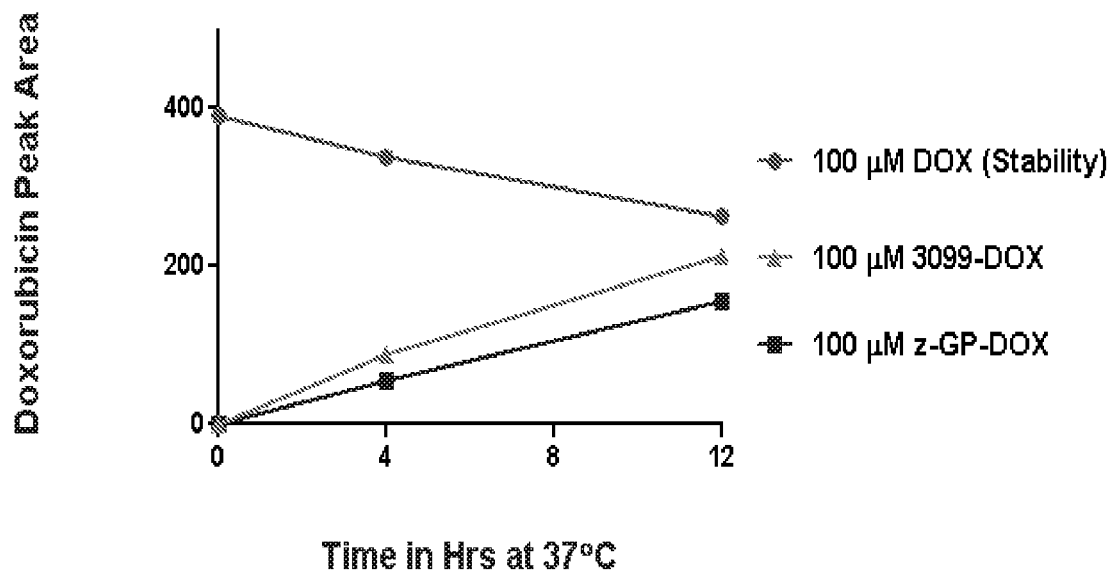
FIG. 5 is a graph depicting in vitro activation of 3099DOX and z-GP-DOX in mouse plasma.

Doxorubicin, 3099DOX, or z-PG-DOX was added to mouse plasma to produce samples containing equimolar final concentrations of 100 μM of drug or prodrug. The resulting samples were then incubated at 37° C. for 12 h, and doxorubicin was measured at 0, 4, and 12 h. Results are shown in FIG. 5. 3099DOX was activated in mouse plasma about 25 percent faster than was z-PG-DOX.

Example 7

Stability of 3099DOX in Mouse Muscle Lysate

Figure 6:
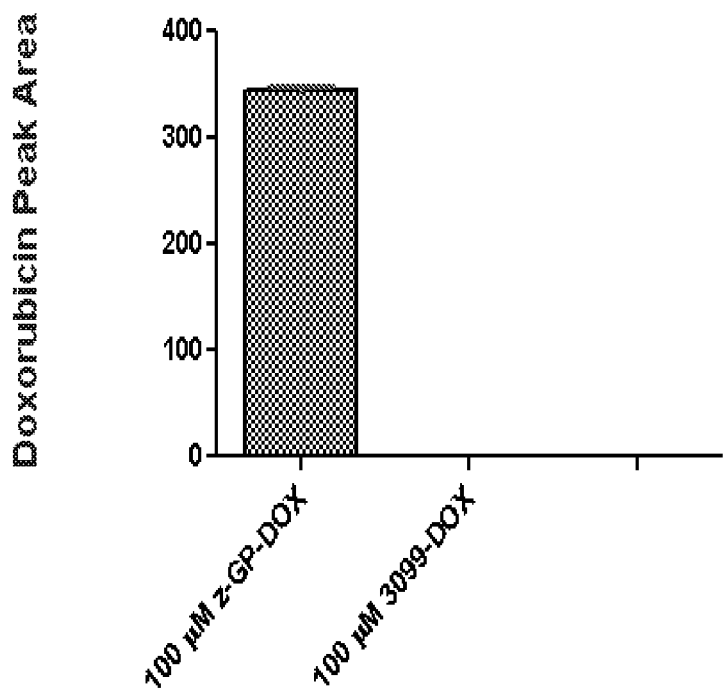
FIG. 6 is a bar graph depicting in vitro stability of 3099DOX in normal mouse muscle lysate. Data for z-GP-DOX is shown for comparison. Data shown is following 12 h digestion at 37° C.

3099DOX or z-PG-DOX was added to freshly prepared mouse muscle lysate to produce samples containing equimolar final concentrations of 100 μM of prodrug. The resulting samples were then incubated at 37° C. for 12 h, and doxorubicin was measured at 12 h. Results are shown in FIG. 6. 3099DOX incubated with muscle lysate released essentially no doxorubicin, while z-GP-DOX incubated under the same conditions released a large amount of doxorubicin.

Example 8

Pharmacokinetics of 3099DOX in Normal Mouse

Figure 7:
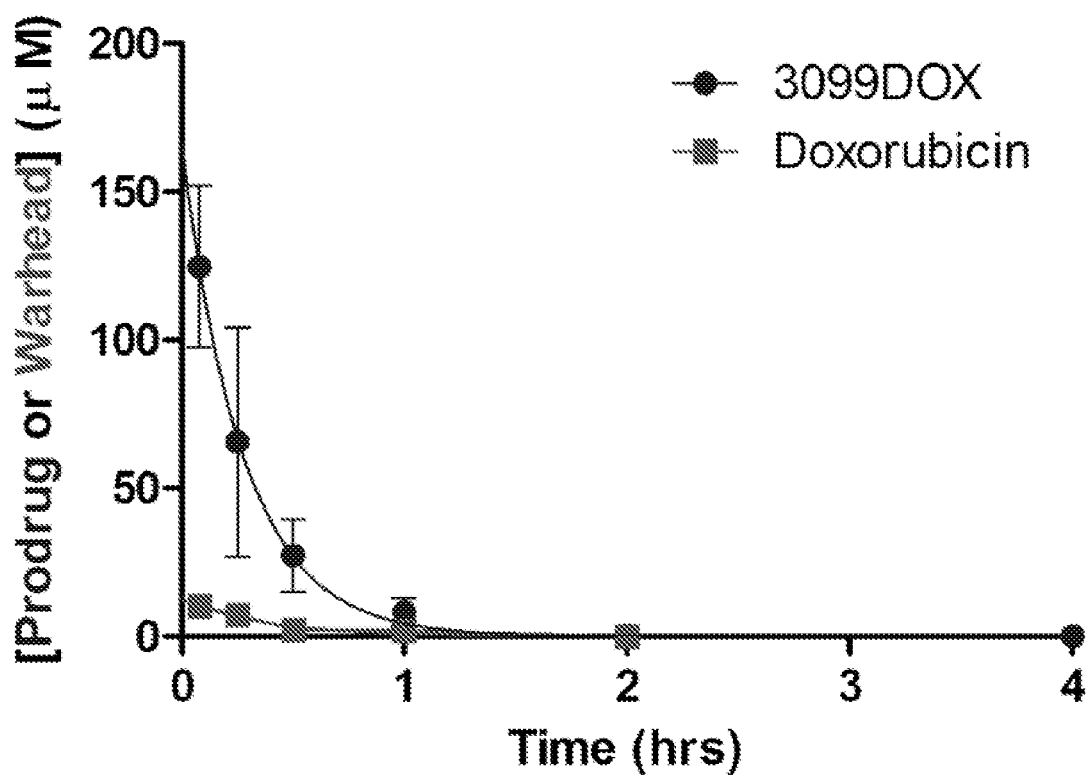
FIG. 7 is a graph depicting pharmacokinetics of 3099DOX ("Prodrug") and doxorubicin ("Warhead") following single administration of 20 mg/kg 3099DOX by iv injection in normal mouse.

Normal, healthy mice were administered 20 mg/kg body weight 3099DOX in a single intravenous (iv) injection. Blood was then collected at 5, 15, 30, 60, 120, and 240 minutes following administration, and plasma was prepared from each blood sample. Plasma concentrations of prodrug (3099DOX) and doxorubicin ("warhead") were measured by LC-MS analysis after protein crash. Results are shown in FIG. 7.

Example 9

Pharmacokinetics of Doxorubicin in Normal Mouse

Figure 8:
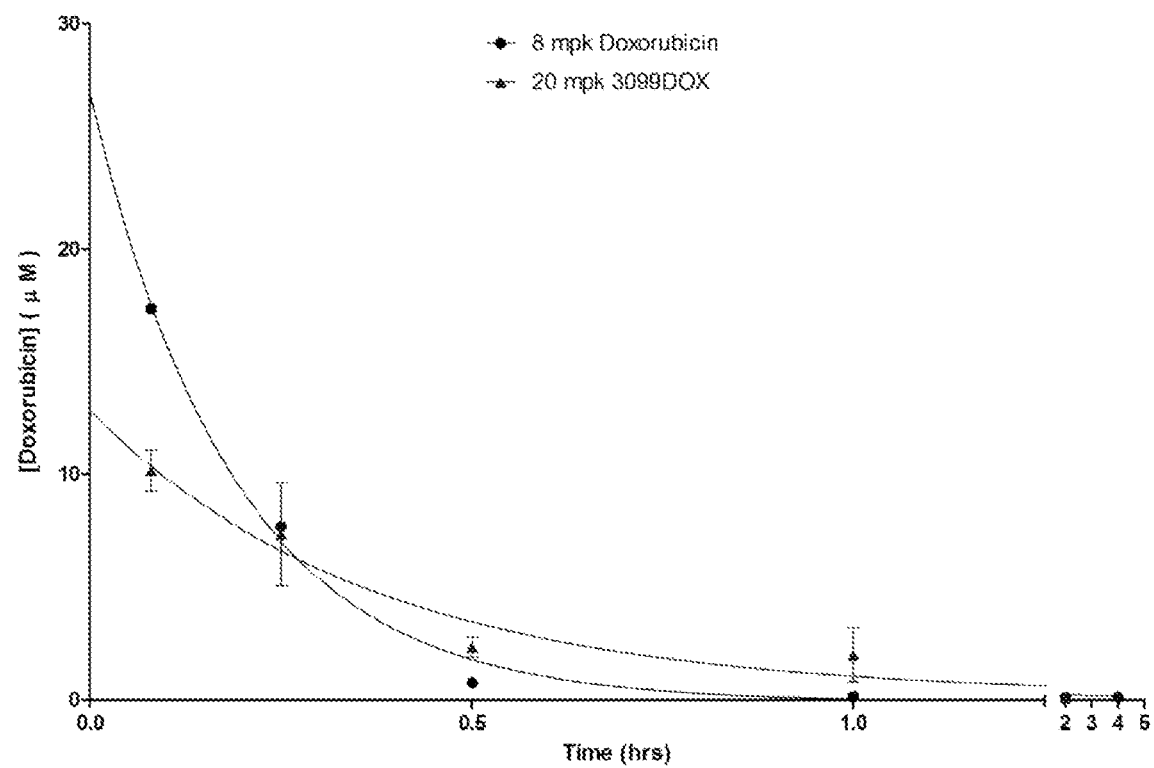
FIG. 8 is a graph depicting in vivo plasma doxorubicin (DOX) concentrations following injection of 20 mg/kg 3099DOX (triangles) or 8 mg/kg doxorubicin (circles); mpk, mg/kg.

Normal, healthy mice were administered either 20 mg/kg body weight 3099DOX or 8 mg/kg body weight doxorubicin in a single intravenous (iv) injection. Blood was then collected at 5, 15, 30, 60, 120, and 240 minutes following administration, and plasma was prepared from each blood sample. Plasma concentrations of doxorubicin were measured by LC-MS analysis after protein crash. Results are shown in FIG. 8.

Example 10

HEK-FAP Tumor Model

Human embryonic kidney (HEK) cells were stably transfected with a mouse FAP or mock vector (Fox Chase Cancer Center, Philadelphia, PA, USA) and cultured in RPMI 1640 cell culture medium without phenol red, supplemented with 2 mM L-glutamine, 10 mM HEPES, 1 mM sodium pyruvate, 4.5 g/L glucose, 100 I.U. penicillin, 100 μg/mL streptomycin and 1% human AB serum (VWR, Radnor, PA, USA).

Mice were then divided into five treatment groups. Treatment started when tumors were 100 mm$^3$ in size. Animals in Group 1 received vehicle alone once per week as a single iv injection. Animals in Group 2 received 2 mg/kg (3.7 mole/kg) doxorubicin once per week as a single iv injection. Animals in Groups 3-5 received 6, 9, or 12 mg/kg (7.4, 11.1, or 14.8 mole/kg) 3099DOX, respectively, once per week as a single iv injection. Tumor size (volume), body weight, and survival were monitored for up to 70 days after starting treatment. Additionally, tissue distribution of 3099DOX and doxorubicin was measured at the end of this study.

Example 11

Tissue Distribution of 3099DOX in the HEK-FAP Tumor Model

Figure 9:
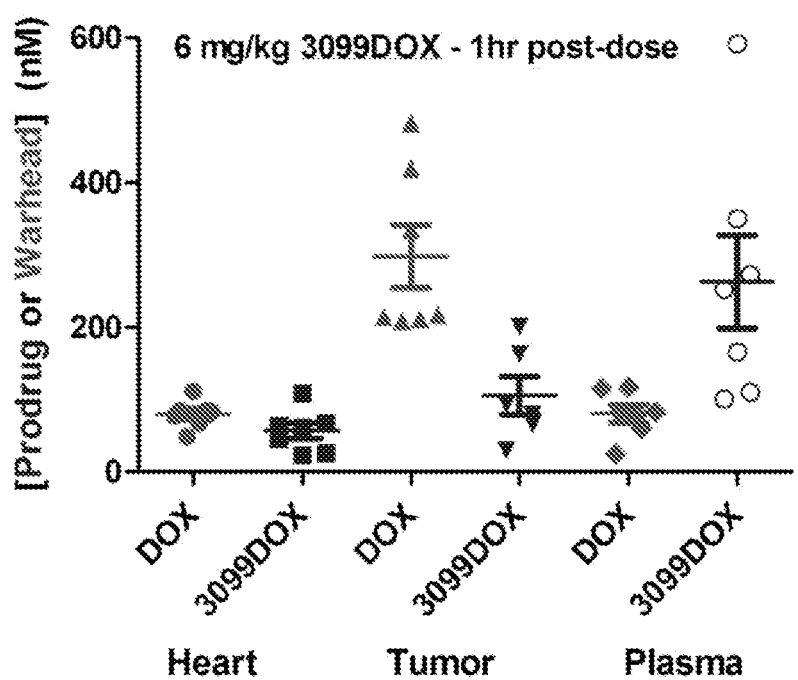
FIG. 9 is a graph depicting in vivo tissue distribution of doxorubicin (DOX; "Warhead") and 3099DOX ("Prodrug") in mice used in the HEK-FAP tumor model study described in the examples. Samples were obtained 1 hour following iv dosing with 6 mg/kg 3099DOX.

Tissues were collected from animals in Group 3 of the HEK-FAP tumor model study described in Example 10 1 hour after the final dose of 3099DOX. Concentrations of 3099DOX (prodrug) and doxorubicin ("warhead") were determined in heart, tumor, and plasma. Results are shown in FIG. 9. Doxorubicin was concentrated in tumor tissue (ca. 300 nM) compared to heart and plasma. 3099DOX was concentrated in plasma (ca. 250 nM) compared to heart and tumor.

Example 12

Efficacy of 3099DOX in the HEK-FAP Tumor Model

Figure 10:
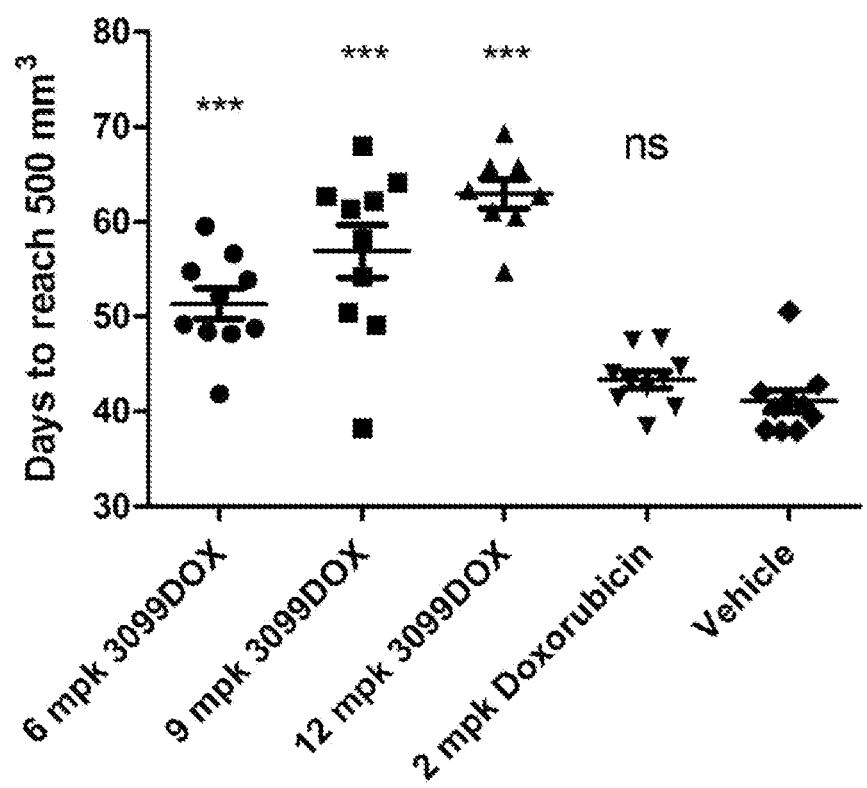
FIG. 10 is a graph depicting in vivo tumor growth in the HEK-FAP tumor model study described in the examples. ***, p<0.05 versus vehicle; ns, not significant versus vehicle; mpk, mg/kg.

Tumor growth was monitored in the HEK-FAP tumor model described in Example 10. Results are shown in FIG. 10. The mean number of days to reach 500 mm$^3$ tumor size was 41 for vehicle-treated controls. The mean number of days to reach 500 mm$^3$ tumor size was 41 43 for doxorubicin-treated Group 2. In striking contrast to either of the former groups, the mean number of days to reach 500 mm$^3$ tumor size was 51, 57, and 63 for 3099DOX-treated Groups 3, 4, and 5, respectively. The latter three values were statistically significant (p<0.05) versus vehicle (Dunnett's multiple comparison test).

Example 13

Efficacy of 3099DOX in the HEK-FAP Tumor Model

Figure 11:
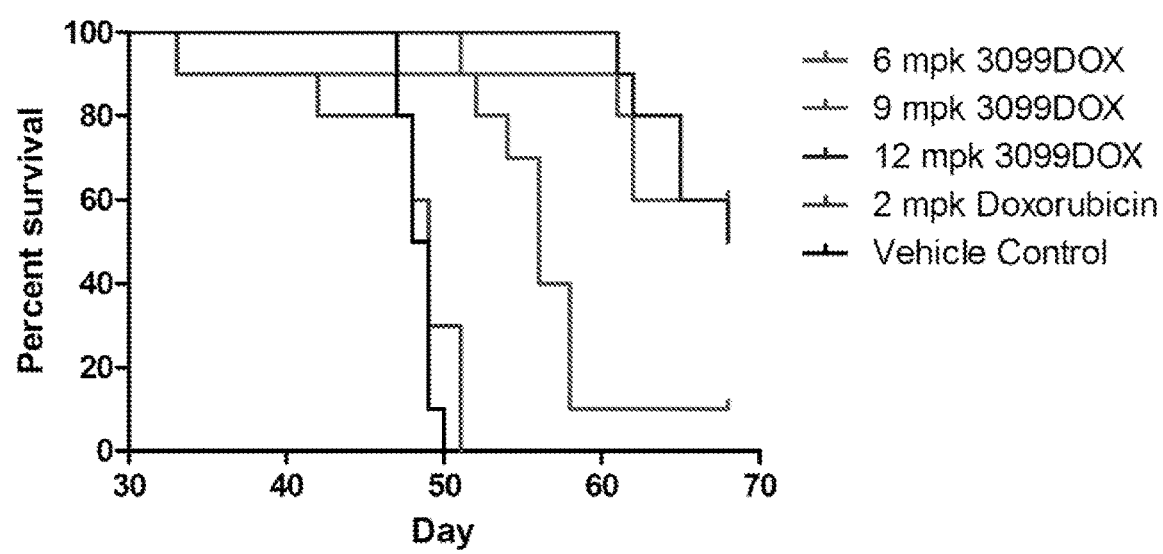
FIG. 11 is a graph depicting survival in the HEK-FAP tumor model study described in the examples; mpk, mg/kg.

Survival was also monitored in the HEK-FAP tumor model described in Example 10. Results are shown in FIG. 11. Animals treated with 3099DOX had significantly longer survival than animals treated with either vehicle alone or doxorubicin. As evident from FIG. 11, survival in the 3099DOX-treated animals was prolonged in a dose-dependent manner.

Example 14

Cytotoxicity of FAP-Activated Doxorubicin Prodrugs Against Various Tumor Lines

Cells from various tumor-derived cell lines were incubated with doxorubicin or 3099DOX, the latter in the presence or absence of FAP, and the EC$_{50}$ for each was determined. Results are shown in the table below.

| Cell Line | DOX | 3099DOX | 3099DOX + 100 μM 3099 | 3099DOX + 25 nM rFAP |
|---|---|---|---|---|
| HEK-Mock | 0.05 | — | 280 | 0.04 |
| HEK-mFAP | 0.2 | 1.1 | 120 | — |
| BxPC-3 | 3.1 | 210 | — | 2.4 |
| HPAF-II | 2.0 | 330 | — | 1.6 |
| HT-29 | 0.4 | 340 | — | 0.8 |

Example 15

Additional FAP-Activated Doxorubicin Prodrugs

| Compound | Structure | Bioassay |
|---|---|---|
| 5057DOX | 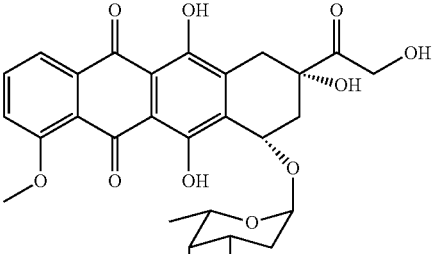 | 1. CellTiter-Blue cell viability assay with HEK-Mock cells:<br>EC50 (prodrug alone) = 480 nM<br>EC50 (prodrug + 25 nM FAP) = 36 nM<br>EC50 (prodrug + 25 nM PREP) = 250 nM<br>EC50 (doxorubicin alone) = 36 nM.<br>Note: This assay involved a 72 hour, rather than the typical 48 hour, incubation of prodrug with the cells prior to addition of the CellTiter-Blue reagent.<br>2. CellTiter-Blue cell viability assay with HEK-Mock and HEK-mFAP cells:<br>HEK-Mock<br>EC50 (prodrug alone) = 460 nM<br>EC50 (prodrug + 25 nM FAP) = 26 nM<br>EC50 (prodrug + 25 nM PREP) = 220 nM<br>EC50 (prodrug + 100 uM 2054-9) = 9.8 uM<br>EC50 (doxorubicin alone) = 34 nM<br>HEK-mFAP<br>EC50 (prodrug alone) = 140 nM<br>EC50 (prodrug + 100 uM 3099-15) = >10 uM<br>EC50 (prodrug + 25 nM PREP) = 110 nM<br>EC50 (prodrug + 100 uM 2054-9) = 740 nM<br>EC50 (doxorubicin alone) = 59 nM.<br><br>Note: This assay involved a 72 hour, rather than the typical 48 hour, incubation of prodrug with the cells prior to addition of the CellTiter-Blue reagent.<br>3. CellTiter-Blue cell viability assay with HEK-Mock and HEK-mFAP cells:<br>HEK-Mock<br>EC50 (prodrug alone) = 2.3 uM<br>EC50 (prodrug + 100 uM 2054-9) = >10 uM<br>EC50 (prodrug + 100 uM 3099-15) = >100 uM<br>EC50 (doxorubicin alone) = 95 nM<br>HEK-mFAP<br>EC50 (prodrug alone) = 600 nM<br>EC50 (prodrug + 100 uM 2054-9) = 5.3 uM<br>EC50 (prodrug + 100 uM 3099-15) = >100 uM<br>EC50 (doxorubicin alone) = 240 nM.<br>Note: This assay involved a 72 hour, rather than the typical 48 hour, incubation of prodrug with the cells prior to addition of the CellTiter-Blue reagent.<br>4. CellTiter-Blue cell viability assay with HEK-Mock and HEK-mFAP cells:<br>HEK-Mock<br>EC50 (prodrug alone) = 1.1 uM<br>EC50 (prodrug + 100 uM 5057) = >100 uM<br>EC50 (doxorubicin alone) = 92 nM<br>HEK-mFAP<br>EC50 (prodrug alone) = 770 nM<br>EC50 (prodrug + 100 uM 5057) = >100 uM<br>EC50 (doxorubicin alone) = 420 nM.<br>Note: This assay involved a 72 hour, rather than the typical 48 hour, incubation of prodrug with the cells prior to addition of the CellTiter-Blue reagent. |

| Compound | Structure | Bioassay |
|---|---|---|
| | | 5. CellTiter-Blue cell viability assays:<br>MCF-7<br>EC50 (prodrug alone) = >100 uM<br>EC50 (prodrug + 25 nM FAP) = 23 uM<br>EC50 (prodrug + 100 uM 5057) = >100 uM<br>EC50 (doxorubicin alone) = 54 uM<br>OVCAR-3<br>EC50 (prodrug alone) = >100 uM<br>EC50 (prodrug + 25 nM FAP) = 1 uM<br>EC50 (prodrug + 100 uM 5057) = >100 uM<br>EC50 (doxorubicin alone) = 1.7 uM<br>SK-OV-3<br>EC50 (prodrug alone) = 830 nM<br>EC50 (prodrug + 25 nM FAP) = 140 nM<br>EC50 (prodrug + 100 uM 5057) = 56 uM<br>EC50 (doxorubicin alone) = 440 nM.<br>Note: This assay involved a 72 hour, rather than the typical 48 hour, incubation of prodrug with the cells prior to addition of the CellTiter-Blue reagent.<br>6. FAP digest of 5057DOX:<br>[FAP] $4.00 \times 10^{-9}$M<br>Vmax $5.19 \times 10^{-9}$M/sec<br>Km $1.11 \times 10^{-5}$M<br>Kcat(Vmax/[E]) 1.30 sec$^{-1}$<br>kcat/Km $1.17 \times 10^5 M^{-1} sec^{-1}$<br>Note: This assay involved a 72 hour, rather than the typical 48 hour, incubation of prodrug with the cells prior to addition of the CellTiter-Blue reagent.<br>7. FAP digest of 5057DOX and 3099DOX:<br>Dox standards; Daunorubicin internal standard<br>[FAP] 1 nM<br>Vmax $9.80 \times 10^{-10}$M/sec<br>Km $4.85 \times 10^{-6}$M<br>Kcat 0.98 sec$^{-1}$<br>Kcat/Km $2.00 \times 10^5 M^{-1} sec^{-1}$<br>Note: This assay involved a 72 hour, rather than the typical 48 hour, incubation of prodrug with the cells prior to addition of the CellTiter-Blue reagent.<br>8. CellTiter-Blue cell viability assay with HEK-mFAP cells:<br>EC50 (prodrug alone) = 1.1 uM<br>EC50 (prodrug + 100 uM 5057) = >100 uM<br>EC50 (doxorubicin) = 400 nM<br>Note: This assay involved a 72 hour incubation of prodrug with the cells prior to addition of the CellTiter-Blue reagent. |
| 5107DOX | 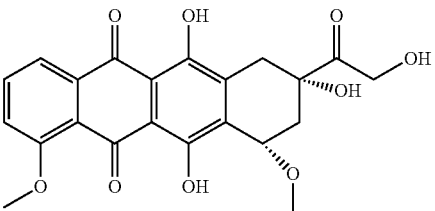 | CellTiter-Blue cell viability assay with HEK-mFAP cells:<br>EC50 (prodrug alone) = 940 nM<br>EC50 (prodrug + 100 uM 5057-2) = >100 uM<br>EC50 (doxorubicin) = 390 nM<br>Note: This assay was performed with a 72 hour incubation of the compounds with the cells prior to addition of the CellTiter-Blue reagent |

-continued

| Compound | Structure | Bioassay |
|---|---|---|
| 5061DOX | 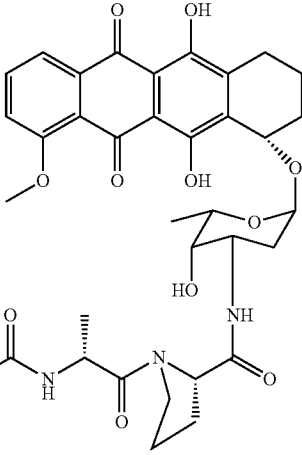 | 1. CellTiter-Blue cell viability assay with HEK-Mock and HEK-mFAP cells:<br>HEK-Mock<br>EC50 (prodrug alone) = >100 uM<br>EC50 (prodrug + 100 uM 5057) = >100 uM<br>EC50 (prodrug + 25 nM FAP) = 280 nM<br>EC50 (prodrug + 50 nM PREP) = >100 uM<br>EC50 (doxorubicin alone) = 92 nM<br>HEK-mFAP<br>EC50 (prodrug alone) = >100 uM<br>EC50 (prodrug + 100 uM 5057) = >100 uM<br>EC50 (doxorubicin alone) = 420 nM.<br>Note: This assay involved a 72 hour, rather than the typical 48 hour, incubation of prodrug with the cells prior to addition of the CellTiter-Blue reagent.<br>2. CellTiter-Blue cell viability assays:<br>HEK-Mock<br>EC50 (prodrug alone) = >100 uM<br>EC50 (prodrug + 25 nM FAP) = 250 nM<br>HEK-mFAP<br><br>EC50 (prodrug alone) = >100 uM<br>EC50 (prodrug + 100 uM 5057) = >100 uM<br>MCF-7<br>EC50 (prodrug alone) = >100 uM<br>EC50 (prodrug + 25 nM FAP) = >100 uM<br>EC50 (prodrug + 100 uM 5057) = >100 uM<br>EC50 (doxorubicin alone) = 54 uM<br>OVCAR-3<br>EC50 (prodrug alone) = >100 uM<br>EC50 (prodrug + 25 nM FAP) = 1.5 uM<br>EC50 (prodrug + 100 uM 5057) = >100 uM<br>EC50 (doxorubicin alone) = 1.7 uM<br>SK-OV-3<br>EC50 (prodrug alone) = >100 uM<br>EC50 (prodrug + 25 nM FAP) = 900 nM<br>EC50 (prodrug + 100 uM 5057) = >100 uM<br>EC50 (doxorubicin alone) = 440 nM.<br>Note: All assays involved a 72 hour, rather than the typical 48 hour, incubation of prodrug with the cells prior to addition of the CellTiter-Blue reagent.<br>3. Inhibition of FAP activity on HEK-mFAP cells:<br>IC50 = >10 uM. |

Example 16

Selectivity of FAP Over PREP

Figure 12:
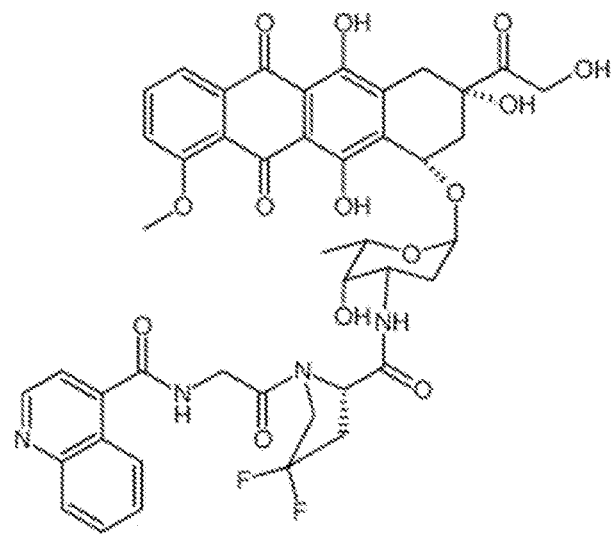
FIG. 12 shows the structure of doxorubicin prodrug 5057DOX, and a graph showing that the doxorubicin prodrug is selectively activated by FAP as compared to PREP.
Figure 12:
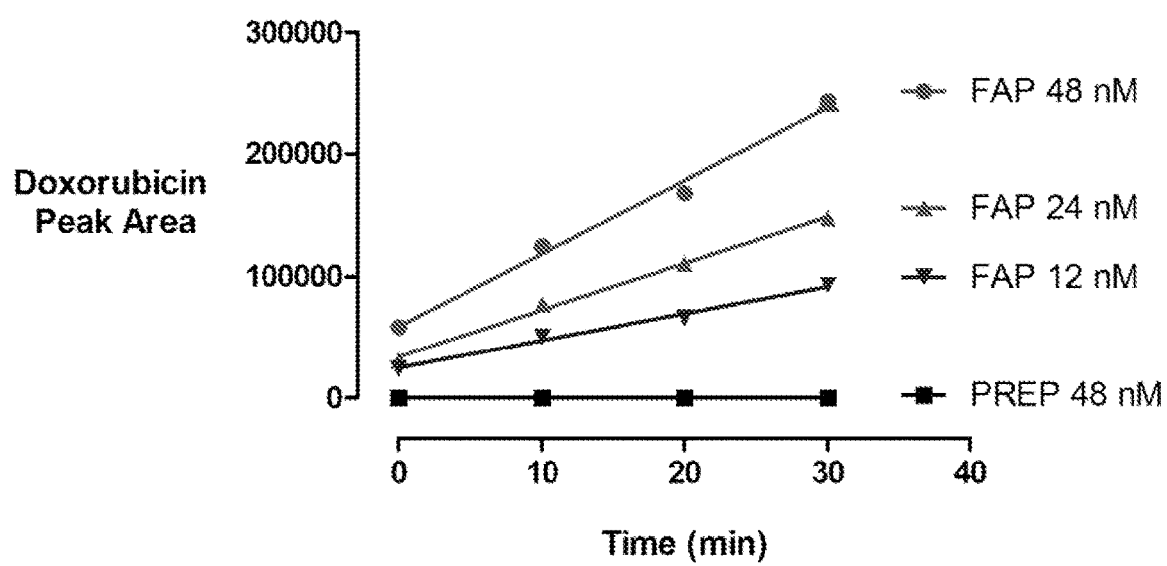
Figure 13A:
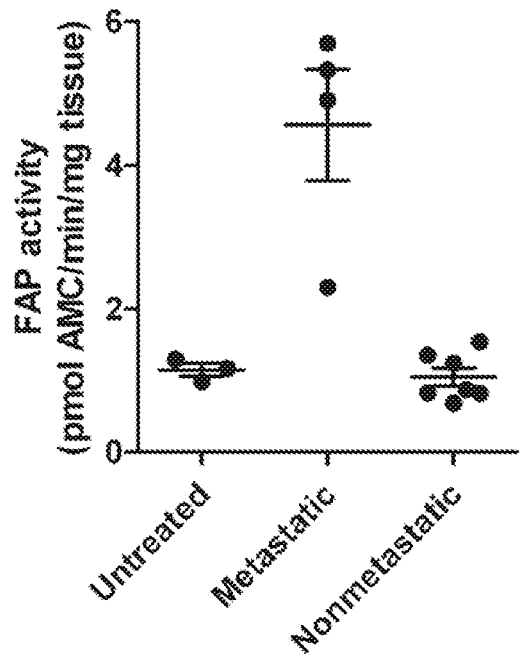
FIG. 13A is a graph depicting FAP activity in mouse liver metastases.
Figure 13B:
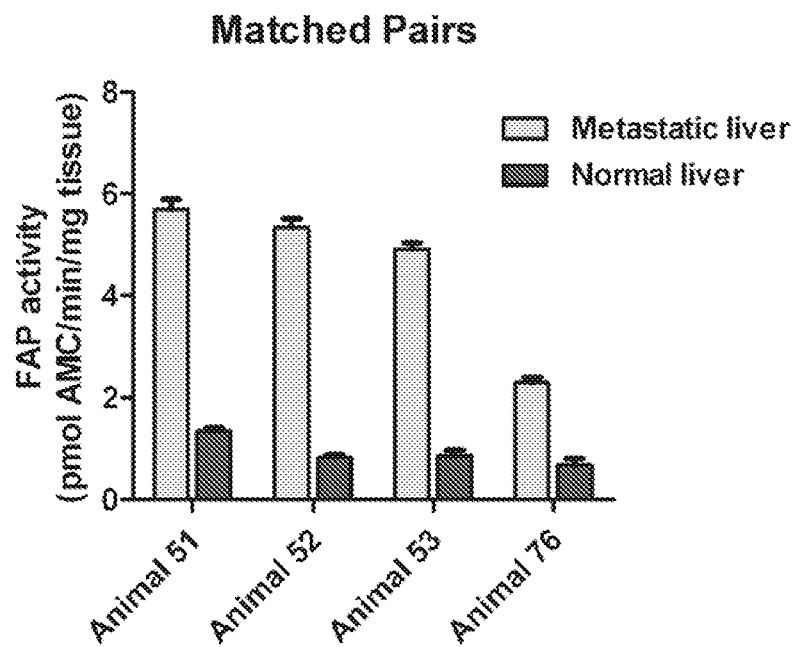
FIG. 13B is a graph depicting FAP activity in mouse liver metastases.
Figure 14A:
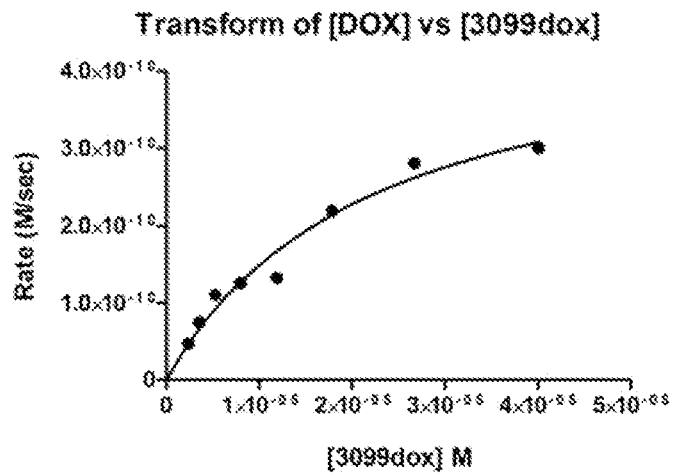
FIG. 14A is a graph depicting activation kinetics for 3099DOX.
Figure 14B:
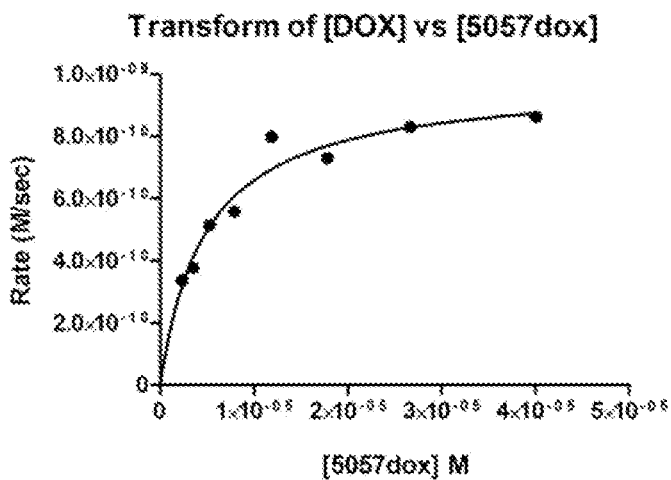
FIG. 14B is a graph depicting activation kinetics for 5057DOX.
Figure 15:
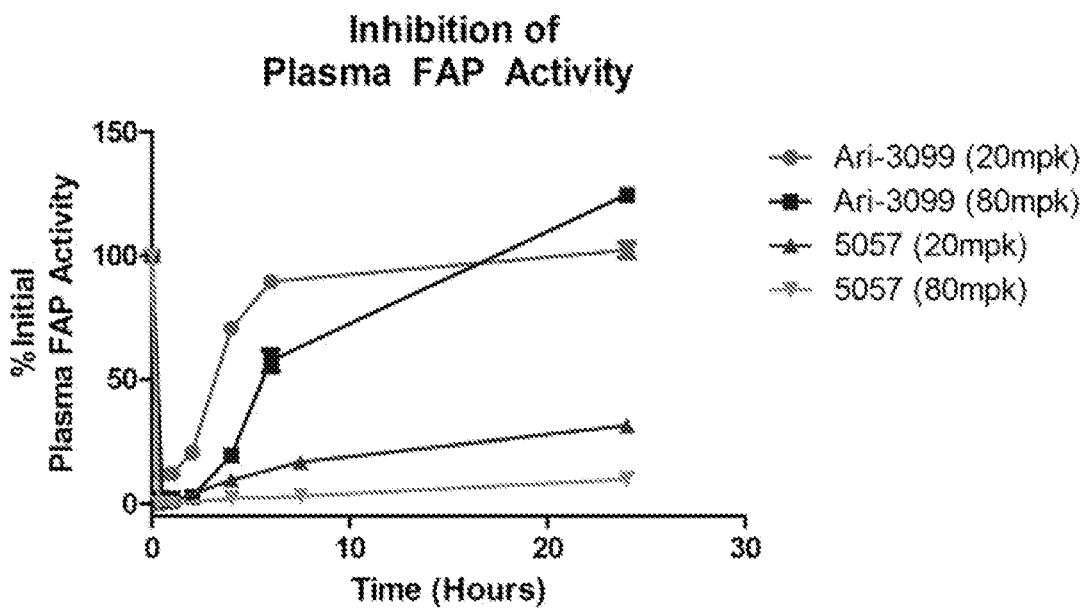
FIG. 15 is a graph depicting pharmacodynamics of inhibition of plasma FAP activity by 3099DOX and 5057DOX. Circles, 20 mg/kg 3099DOX; squares, 80 mg/kg 3099DOX; triangles, 20 mg/kg 5057DOX; inverted triangles, 80 mg/kg 5057DOX.
Figure 16A:
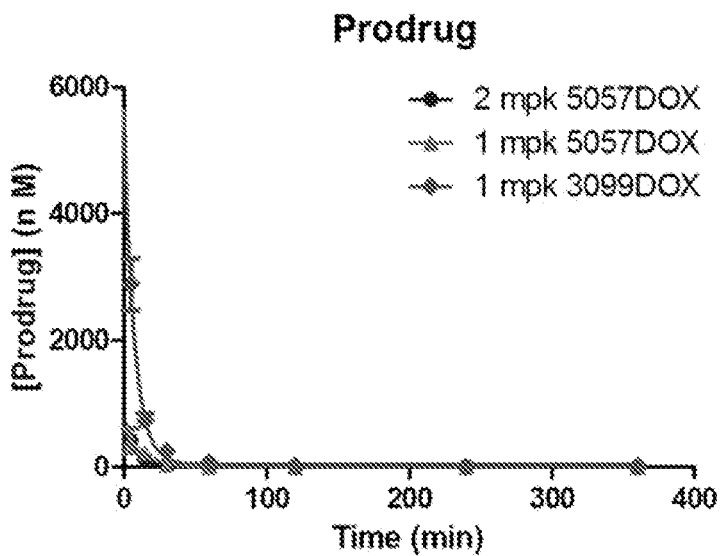
FIG. 16A is graph depicting plasma pharmacokinetics of prodrug in normal mice treated with the indicated doses of 5057DOX or 3099DOX; mpk, mg/kg.
Figure 16B:
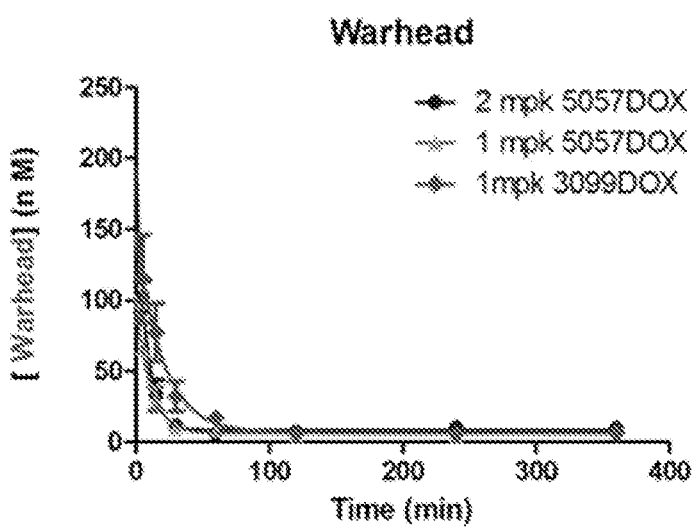
FIG. 16B is graph depicting plasma pharmacokinetics of "warhead" in normal mice treated with the indicated doses of 5057DOX or 3099DOX; mpk, mg/kg.

Recombinant enzyme (FAP or PREP) was combined, at reaction concentration of 12 nM, 24 nM, or 48 nM, with 240 nM 5057DOX in FAP buffer (50 mM Tris-HCl, pH 7.4, 140 mM NaCl) and incubated at 37° C. Reactions were stopped at 0, 10, 20, or 30 minutes by addition of equal volume of 10 μM Val-boroPro (FAP inhibitor). Doxorubicin was measured by liquid chromatography/mass spectroscopy (LCMS). Representative results are shown in FIG. 12.

Example 17

Tissue Distribution of 5057DOX in HEK-FAP Mice

Figure 17:
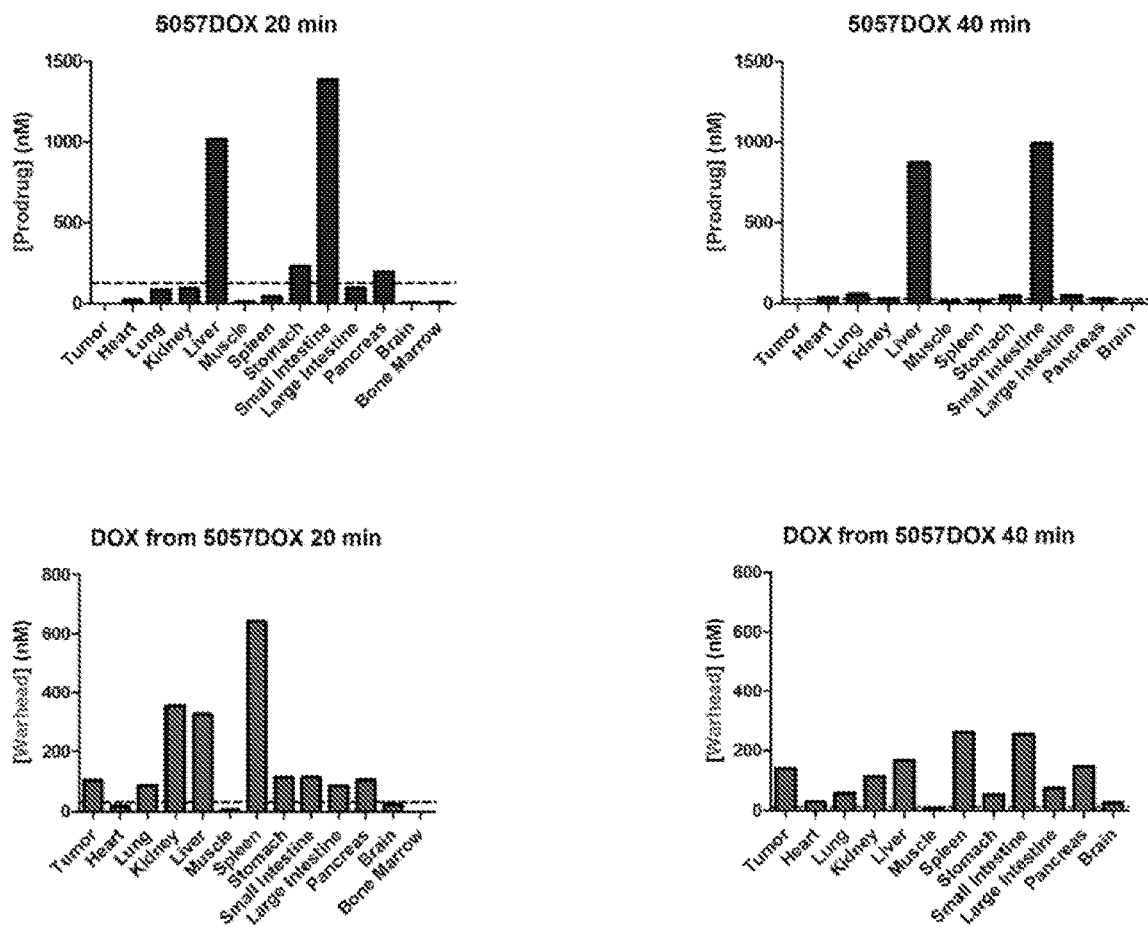
FIG. 17 is four graphs depicting tissue distribution of 5057DOX and "warhead" in tumor-bearing HEK-FAP mice at the indicated times following intravenous injection with 2 mg/kg of 5057DOX. Dashed lines represent approximate plasma concentrations of 5057DOX or "warhead" derived from pharmacokinetic studies in normal mice.

Tumor-bearing HEK-FAP mice were administered 2 mg/kg 5057DOX by intravenous injection. Mice were then euthanized 20 or 40 min following administration of 5057DOX and tissues were collected for analysis. Tumor, heart, lung, kidney, liver, muscle, spleen, stomach, small intestine, large intestine, pancreas, brain, and bone marrow tissues separately were placed into lysis buffer, homogenized, vortexed, incubated on wet ice for 40 min, sonicated 3 times for 3 sec, centrifuged for 30 min at 4° C., and then lysates analyzed for prodrug and "warhead". Representative results are shown in FIG. 17.

Example 18

Efficacy of 5057DOX in HEK-FAP Mice

Figure 18:
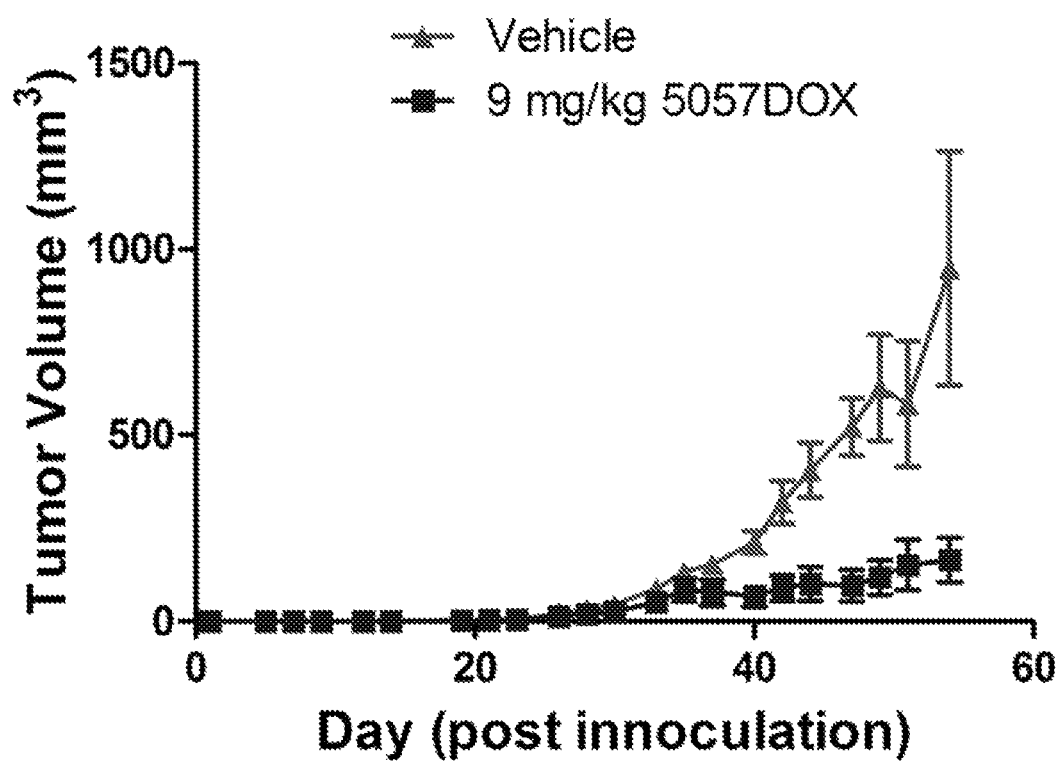
FIG. 18 is a graph depicting efficacy of 9 mg/kg 5057DOX vs. vehicle in HEK-FAP mice, where animals with tumors >200 mm³ on day 33 post inoculation (i.e., at start of treatment) are excluded.
Figure 19:
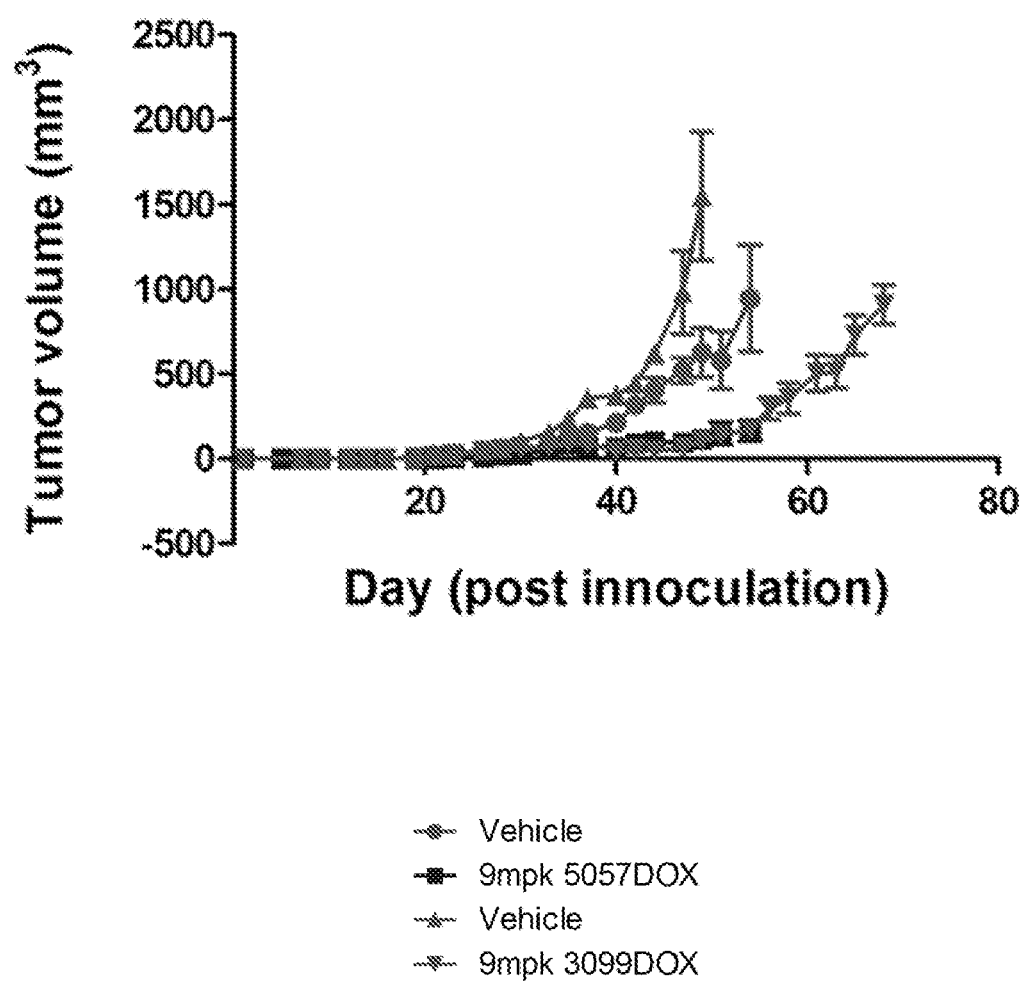
FIG. 19 is a graph depicting efficacy of 9 mg/kg 5057DOX (squares) vs. vehicle and efficacy of 9 mg/kg 3099DOX (inverted triangles) vs. vehicle HEK-FAP mice, where animals with tumors >200 mm³ on day 33 post inoculation (i.e., at start of treatment) are excluded.

HEK-FAP mice were administered 9 mg/kg 5057DOX or vehicle control by intravenous injection on day 33 after inoculation with tumor. Tumor volumes were monitored daily. Representative results for mice with tumor volumes less than 200 mm$^3$ on day 33 (i.e., on the day of treatment with 5057DOX) are shown in FIG. 18. Comparative data for 3099DOX is shown in FIG. 19.

INCORPORATION BY REFERENCE

All U.S. patents and U.S. and PCT published patent applications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

We claim:

1. A method of treating a disorder in which fibroblast activation protein (FAP) is upregulated, comprising administering to a subject in need thereof a therapeutically effective amount of:
(i) a prodrug represented by Formula I:

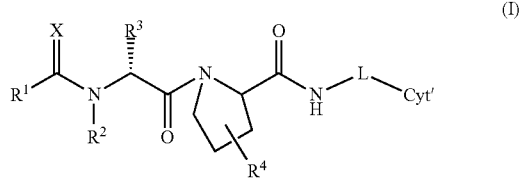

(I)

or a pharmaceutically acceptable salt thereof, wherein:
$R^1$ represents $(C_1-C_{10})$alkyl, $(C_1-C_{10})$alkoxy, $(C_1-C_{10})$alkyl-C(O)—$(C_1-C_{10})$alkyl, $(C_3-C_3)$cycloalkyl, $(C_3-C_3)$cycloalkyl$(C_1-C_{10})$alkyl, aryl, aryl$(C_1-C_{10})$alkyl, heteroaryl, or heteroaryl$(C_1-C_{10})$alkyl, wherein any $R^1$ is optionally substituted with one or more substituents independently selected from the group consisting of halo, hydroxy, carboxylate, cyano, amino, nitro, and —SH; or

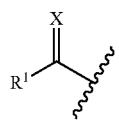

represents an N-terminally blocked alpha amino acid residue, wherein X is O;
$R^2$ represents H or a $(C_1-C_6)$alkyl;
$R^3$ represents a $(C_1-C_6)$alkyl;
$R^4$ is absent or represents a $(C_1-C_6)$alkyl, —OH, —NH$_2$, or halogen;
X represents O or S;
L represents a bond, or —N(H)-L- represents a self-immolative linker; and
Cyt' represents a radical of an anthracycline or derivative thereof; and
(ii) an additional therapeutic agent.

2. The method of claim 1, wherein L is a bond.
3. The method of claim 1, wherein the anthracycline or derivative thereof is doxorubicin.
4. The method of claim 1, wherein $R^2$ is H.
5. The method of claim 1, wherein $R^3$ is methyl.
6. The method of claim 1, wherein —C(X)R$^1$ is a moiety which, at physiological pH, reduces cell permeability of the prodrug relative to the anthracycline or derivative thereof.

7. The method of claim 1, wherein —C(X)R$^1$ comprises one or more functional groups that are ionized at physiological pH.
8. The method of claim 1, wherein —C(X)R$^1$ is selected from the group consisting of aryl$(C_1-C_6)$acyl and heteroaryl$(C_1-C_6)$acyl.
9. The method of claim 1, wherein —C(X)R$^1$ represents an N-terminally blocked alpha amino acid residue, wherein X is O.
10. The method of claim 1, wherein the prodrug is represented by a formula selected from the group consisting of:

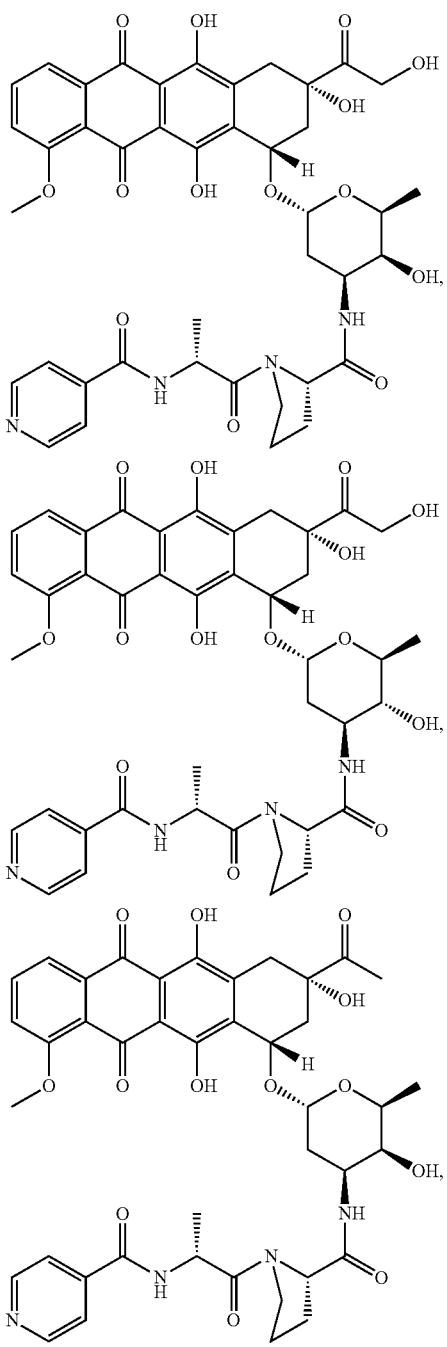

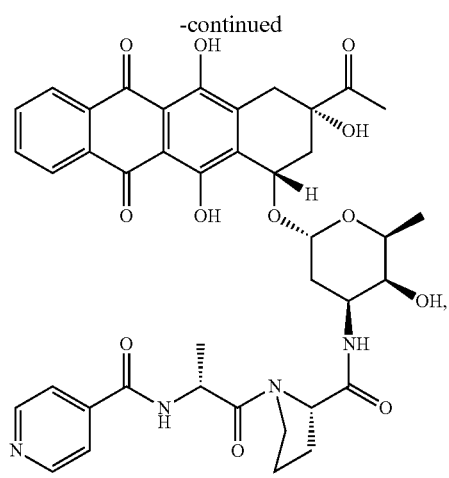

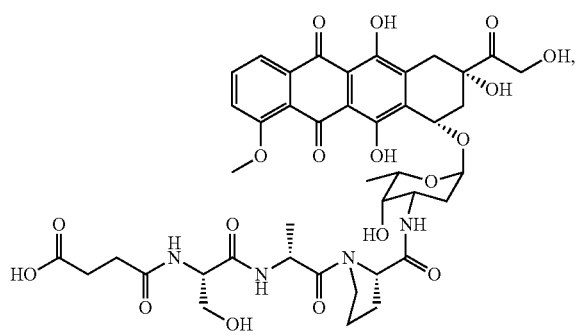

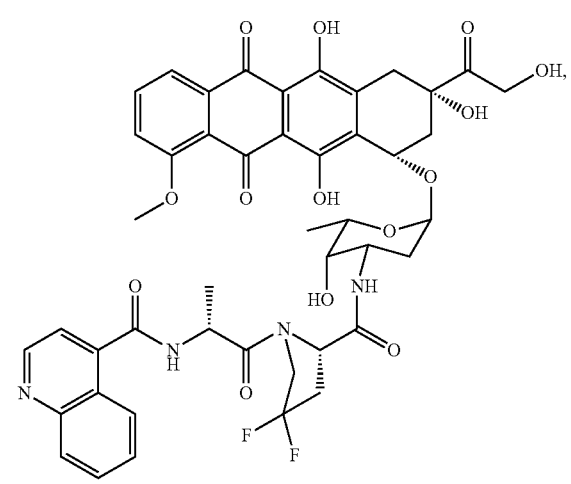

and

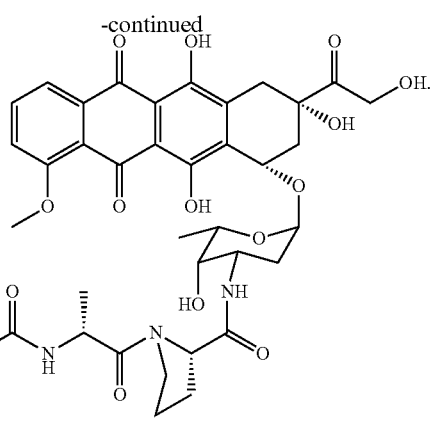

11. The method of claim 1, wherein the prodrug is represented by the formula

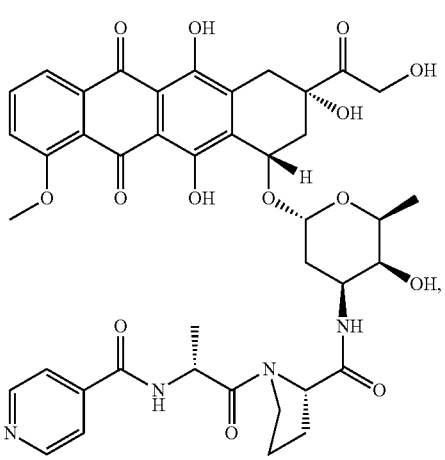

12. The method of claim 1, wherein R⁴ is absent or represents two halogens.

13. The method of claim 1, wherein the disorder is cancer.

14. The method of claim 13, wherein the cancer is breast carcinoma.

15. The method of claim 13, wherein the cancer is soft tissue sarcoma.

16. The method of claim 13, wherein the additional therapeutic agent is a chemotherapeutic agent.

17. The method of claim 11, wherein the disorder is cancer.

18. The method of claim 17, wherein the cancer is breast carcinoma.

19. The method of claim 17, wherein the cancer is soft tissue sarcoma.

20. The method of claim 17, wherein the additional therapeutic agent is a chemotherapeutic agent.

* * * * *